United States Patent
Hyland et al.

(10) Patent No.: US 7,972,487 B2
(45) Date of Patent: Jul. 5, 2011

(54) MICRO-BAND ELECTRODE

(75) Inventors: Mark Hyland, Oxfordshire (GB); Kevin Lorimer, Oxfordshire (GB); Ronald Neil Butler, Oxfordshire (GB); Emma Naomi Kathlene Wallace-Davis, Oxfordshire (GB); Yann Astier, Oxfordshire (GB)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1101 days.

(21) Appl. No.: 10/499,129

(22) PCT Filed: Dec. 23, 2002

(86) PCT No.: PCT/GB02/05911
§ 371 (c)(1),
(2), (4) Date: Mar. 30, 2005

(87) PCT Pub. No.: WO03/056319
PCT Pub. Date: Jul. 10, 2003

(65) Prior Publication Data
US 2005/0178674 A1    Aug. 18, 2005

(30) Foreign Application Priority Data

Dec. 21, 2001   (GB) .................................. 0130684.4

(51) Int. Cl.
*C12Q 1/00*     (2006.01)
*C12Q 1/26*     (2006.01)

(52) U.S. Cl. ......... 204/403.14; 204/403.13; 204/403.01; 204/403.09; 205/775

(58) Field of Classification Search .................. 205/775; 204/403.14, 403.13, 403.01, 403.09
See application file for complete search history.

(56) References Cited

U.S. PATENT DOCUMENTS

| | | |
|---|---|---|
| 4,734,184 A | 3/1988 | Burleigh et al. |
| 5,120,420 A | 6/1992 | Nankai et al. |
| 5,512,489 A | 4/1996 | Girault et al. |
| 5,725,747 A | 3/1998 | Pinkowski et al. |
| 5,739,039 A | 4/1998 | Girault et al. |
| 5,863,400 A | 1/1999 | Drummond et al. |

(Continued)

FOREIGN PATENT DOCUMENTS

EP          0 653 629 A2    5/1995
(Continued)

OTHER PUBLICATIONS

Aguilar, Z. P., et al., "Self-Contained Microelectrochemical Immunoassay for Small Volumes Using Mouse IgG as a Model System", Analtyical Chemistry, vol. 74, No. 14, Jul. 15, 2002, p. 3321-3329.*

(Continued)

*Primary Examiner* — Ula C Ruddock
*Assistant Examiner* — J. Christopher Ball
(74) *Attorney, Agent, or Firm* — Quarles & Brady LLP; George E. Haas

(57) ABSTRACT

The invention concerns an electrochemical cell which, either alone or together which a substrate onto which it is placed, is in the form of a receptacle. The electrochemical cell contains a working electrode and a counter electrode, the working electrode being in a wall of the receptacle. At least one of the electrodes has at least one dimension of less than 50 μm. The electrochemical cell is principally intended for use as a micro-electrode suitable for screening water, blood, urine or other biological or non-biological fluids.

35 Claims, 16 Drawing Sheets

U.S. PATENT DOCUMENTS

| | | | |
|---|---|---|---|
| 6,110,354 A * | 8/2000 | Saban et al. | 205/775 |
| 6,214,612 B1 | 4/2001 | Yamamoto et al. | |
| 6,287,517 B1 * | 9/2001 | Ackley et al. | 422/68.1 |
| 7,144,486 B1 * | 12/2006 | Fritsch et al. | 204/403.06 |
| 2002/0058279 A1 * | 5/2002 | Fritsch et al. | 435/6 |
| 2002/0092612 A1 | 7/2002 | Davies et al. | |

FOREIGN PATENT DOCUMENTS

| | | |
|---|---|---|
| EP | 1 124 131 | 8/2001 |
| EP | 1 150 118 | 10/2001 |
| EP | 0 884 392 | 12/2002 |
| EP | 1 347 292 | 9/2003 |
| GB | 2244135 | 11/1991 |
| WO | WO 97/00441 | 1/1997 |
| WO | WO 98/43074 | 10/1998 |
| WO | WO 99/46585 | 9/1999 |
| WO | WO 99/60392 | 11/1999 |
| WO | WO 01/13102 | 2/2001 |
| WO | WO 02/06806 | 1/2002 |
| WO | WO 02/076160 | 9/2002 |

OTHER PUBLICATIONS

Henry, C. S., and I. Fritsch, "Microcavities Containing Individually Addressable Recessed Microdisk and Tubular Nanoband Electrodes", Journal of the Electrochemical Society, vol. 146, No. 9, 1999, p. 3367-3373.*

J. Christopher Ball, et al.,"Effect of Fabrication Factors on Performance of Screen-Printed/Laser Micromachined Electrochemical Nanovials," Electroanalysis, pp. 685-690, 2000, vol. 12, No. 9.

Search Report with a date of mailing of Jun. 25, 2003, corresponding to PCT/GB02/05911.

J. Christopher Ball, et al., "Electrochemistry in Nanovials Fabricated by Combining Screen Printing and Laser Micromachining," Analytical Chemistry, Feb. 1, 2000, pp. 497-501, vol. 72, No. 3. 2000 American Chemical Society, published on Web Dec. 28, 1999.

\* cited by examiner

FIG. 7
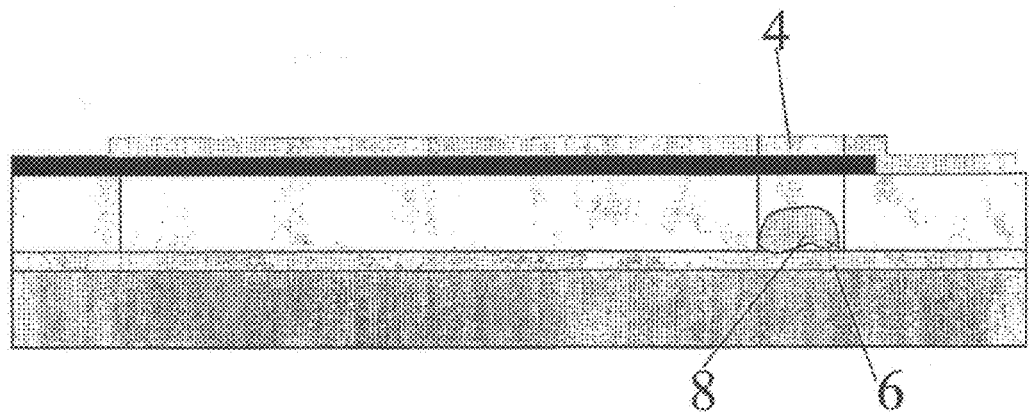
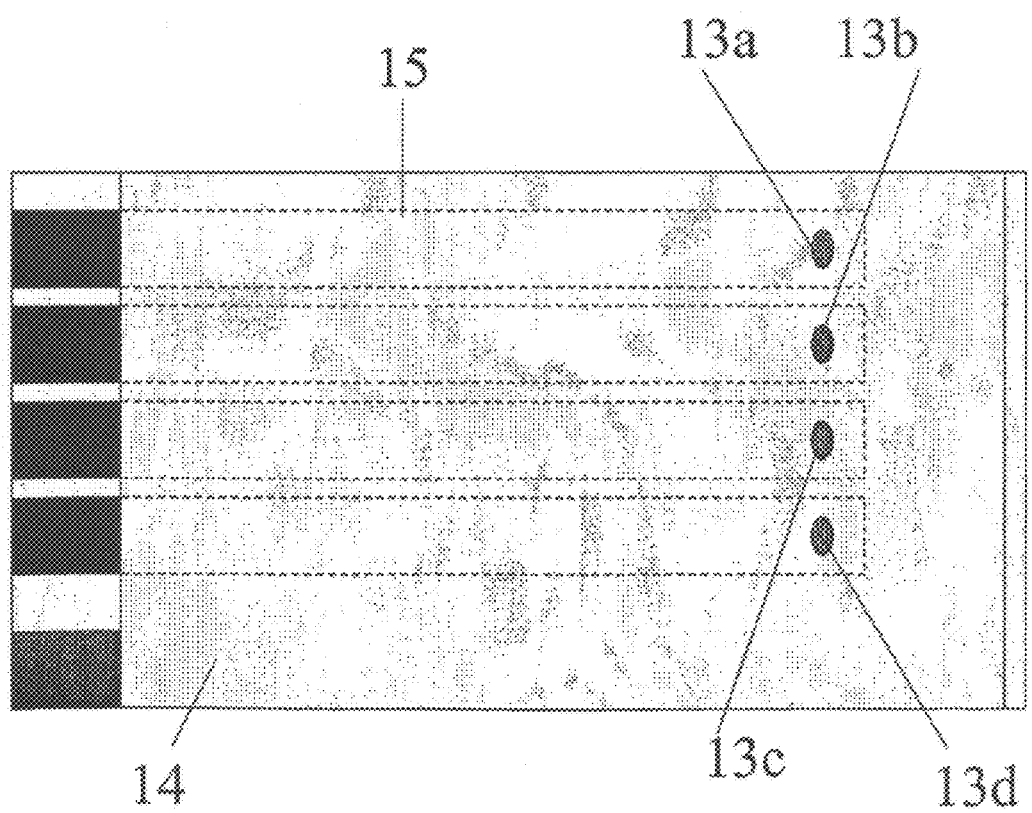

FIG. 9
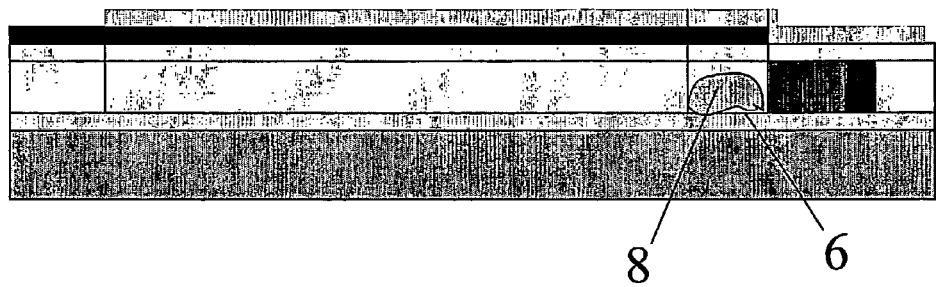
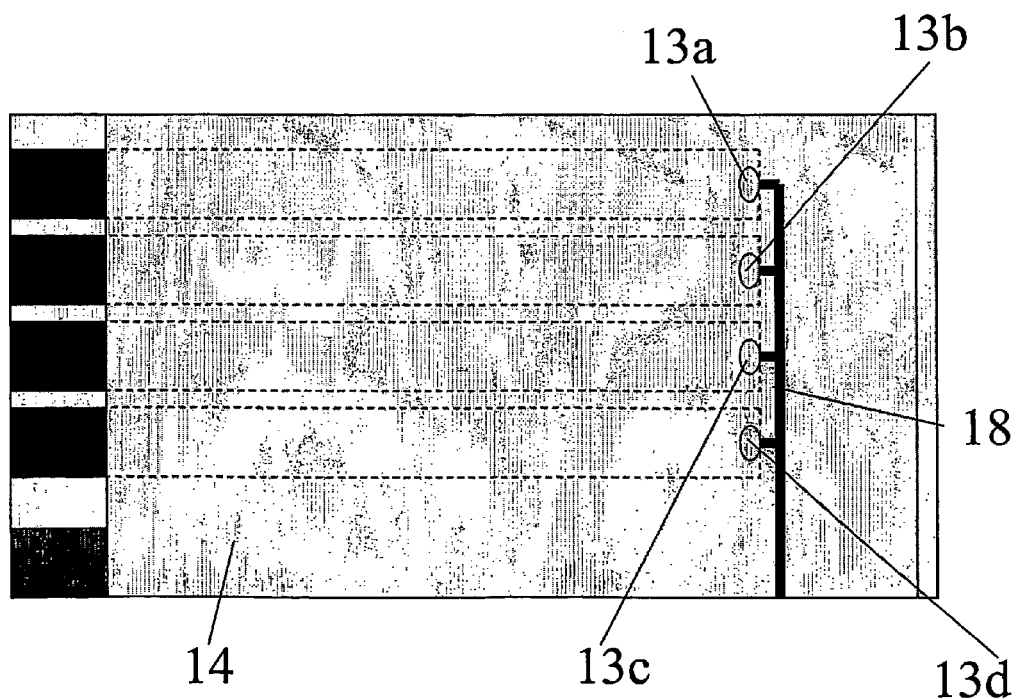

MICRO-BAND ELECTRODE

FIELD OF THE INVENTION

The present invention relates to an electrochemical cell, typically a micro-electrode for electrochemical detection, a process for manufacturing such a cell and a method for electrochemically testing a substance using the micro-electrode.

BACKGROUND TO THE INVENTION

Micro-electrodes are used for the electrochemical detection of various parameters of a substance. For example, a micro-electrode may be used to detect, or measure the concentration of, a particular compound in a test substance. Typically, micro-electrodes contain an electrode which has at least one dimension which is equal to or less than 50 µm, and frequently a dimension of from 1 to 25 µm. The use of these systems as sampling devices brings a number of potential benefits including speed of operation, accuracy and minimal sample requirement.

The common forms of large scale production fabricated micro-electrodes are either micro-disc, micro-band or inter-digitated electrodes. A micro-disc electrode is a plate like electrode with a diameter of less than about 25 µm whereas the micro-band electrode consists of a stripe with a thickness or smallest dimension of less than about 25 µm. The inter-digitated electrode has a more complex form of two combs with their teeth inter meshed.

By using these micro-electrodes in conjunction with enzymes or other electro-active substances it is possible to create sensors that provide quantitative measurement of target parameters through reactions with the corresponding electro-active substance.

However, several problems occur when using the micro-electrodes known in the art in conjunction with an electro-active substance. Firstly, difficulties are frequently experienced in fixing the electro-active substance to the electrodes and movement of the substance away from its desired location is often seen. Systems containing several micro-electrodes on a single substrate are particularly susceptible to problems in this regard, since enzymes which are not sufficiently attached to their electrode become loose and migrate from one sensor to another causing cross-contamination. This type of problem is exacerbated by the effect of the sample flowing over the micro-electrode, which tends to wash the electro-active substance off the electrode.

A common manner of immobilizing the electro-active substance, at least to some extent, is to dry it in position on the electrode. However, this is typically not sufficient to hold the electro-active substance in place. Furthermore, drying the electro-active substance on top of the micro-electrode can cause electrical fouling of the electrode.

It is therefore an object of the present invention to provide a micro-electrode which is capable of holding an electro-active substance at the electrode ready for sample testing and which will restrict movement of any such electro-active substance whilst the sample flows over the micro-electrode. It is also desired that the problems of electrode fouling which occur when an electro-active substance is dried to the electrodes will be avoided or reduced.

SUMMARY OF THE INVENTION

The present inventors have found that the problems discussed above can be minimised when the micro-electrode is in the form of a receptacle. The receptacle comprises a working electrode in the wall of the receptacle, typically having a small surface area. A counter electrode is also present, this electrode typically having a much larger surface area than that of the working electrode, generally a surface area which is at least an order of magnitude larger than that of the working electrode. The electro-active substance may be placed into the receptacle and is optionally dried into position. The sample is then applied to the receptacle in order that testing can be carried out.

Such a micro-electrode is thus ideally suited to containing the electro-active substance and preventing its movement away from the electrodes. Furthermore, the effect of the sample flowing over the micro-electrode is much reduced and is unlikely to cause the enzyme to be washed away from its position in the base of the receptacle.

The electro-active substance will typically not contact the working electrode in the wall of the receptacle during storage and therefore fouling of this electrode is minimised. Furthermore, the electro-active substance will typically contact only a small proportion of the counter electrode and in some embodiments (discussed below) contact with the counter electrode can be totally avoided. Therefore, if fouling does occur, this will only be to a relatively small area of the electrode. The remaining, unaffected areas of the counter electrode may still operate as normal.

Accordingly the present invention provides an electrochemical cell which, either alone or in combination with a substrate onto which it is placed, is in the form of a receptacle, said cell comprising a counter electrode and a working electrode, wherein at least one electrode has at least one dimension not exceeding 50 µm, the working electrode being in a wall of the receptacle. The present invention in particular provides an electrochemical cell in the form of a receptacle, said cell comprising a counter electrode and a working electrode, wherein at least one electrode has at least one dimension not exceeding 50 µm, the working electrode being in a wall of the receptacle.

The present invention also provides a process for producing an electrochemical cell such as is described above, which process comprises the steps of:
  (a) forming a first part comprising an insulating material which is optionally coated with a counter electrode layer;
  (b) forming a second part comprising a laminate of a working electrode layer between two layers of an insulating material;
  (c) creating a hole in the second part and
  (d) bonding said first part to said second part to form a receptacle.

Where a counter electrode layer is present in the first part, step (d) comprises bonding the counter electrode layer of said first part to said second part to form a receptacle.

The process of the invention provides a simple and efficient way of producing the micro-electrodes of the invention. Furthermore, the step of creating a hole in the part containing the working electrode may eliminate the need for a separate step to activate the carbon, or other working electrode.

The present invention also provides a multi-analyte device which comprises a plurality of micro-electrodes in a single device. This device enables different types of measurement to be taken for a single sample by using different electro-active substances in the various micro-electrodes. Alternatively, the multi-analyte device can be used to carry out the same test on a single sample several times in order to detect or eliminate errors in results. The multi-analyte device of the present invention also ensures complete segregation of different electro-active substances since each micro-electrode is self-contained.

The present invention also provides a method of electrochemically testing a substance, the method comprising the steps of:
(a) insetting the sample into an electrochemical cell or multi-analyte device of the invention;
(b) applying a voltage or a current between the working and counter electrodes of the micro-electrode; and
(c) measuring the resulting current, voltage or charge across the micro-electrode.

BRIEF DESCRIPTION OF THE FIGURES

FIGS. 7, 8 and 9 show a multi-analyte device containing four electrochemical cells of the present invention;

DETAILED DESCRIPTION OF THE INVENTION

An electrochemical cell comprises a working electrode and a counter electrode which are connected to one another electrically. When in use, electrochemical reactions occurring at each of the electrodes cause electrons to flow to and from the electrodes, thus generating a current. An electrochemical cell can be set-up either to harness the electrical current produced, for example in the form of a battery, or to detect electrochemical reactions which are induced by an applied current or voltage.

Embodiment 1

Figure 1:
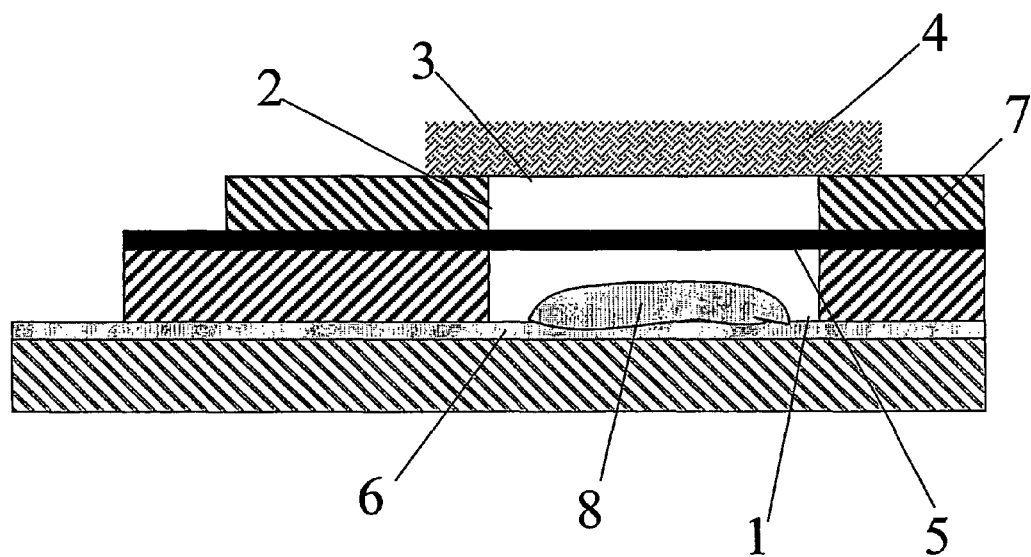
FIG. 1 depicts an electrochemical cell according to a first embodiment of the invention.

A first embodiment of the present invention is depicted in FIG. 1. In this embodiment, the electrochemical cell has a micro-electrode. A micro-electrode has at least one dimension not exceeding 50 μm. Microelectrodes exhibit a typical microelectrode response when using cyclic voltammetry. The microelectrodes of the invention may have one or more dimensions which are macro in size, i.e. which are greater than 50 μm. Due to these macro dimensions, the electrochemical cells of the invention may exhibit some characteristics which are not usually associated with microelectrodes. For example, the electrochemical cells of the invention may exhibit some degree of Cottrell current. For the purposes of the present specification therefore, the term microelectrode is taken to include any electrode have at least one dimension not exceeding 50 μm.

Typically, the micro-electrode will be suitable for screening water (such as river water), blood, urine or other biological fluids or liquids such as beer and wine for determination of their contents. The cell is in the form of a receptacle or a container. The receptacle may be in any shape as long as it is capable of containing a liquid which is placed into it. For example, the receptacle may be cylindrical. Generally, a receptacle will contain a base 1 and a wall or walls 2 which surround the base. In one embodiment of the invention, which is described further below, the cell itself does not have a base and thus is not, alone, a receptacle. However, the cell is designed such that when placed against a separate substrate, the cell together with the substrate forms a receptacle. In this embodiment, the cell comprises a wall or walls 2 which surround an open "base". The open "base" may be placed against the substrate to form a receptacle, such that the substrate forms the true base of the receptacle thus formed.

Typically, the receptacle will have a depth (i.e. from top to base) of from 50 to 1000 μm, preferably from 200 to 800 μm, for example from 300 to 600 μm. The length and width (i.e. from wall to wall), or in the case of a cylindrical receptacle the diameter, of the receptacle is typically from 0.1 to 5 mm, for example 0.5 to 1.5 mm, such as 1 mm.

The open end of the receptacle 3 may be partially covered by an impermeable material as long as at least part of the open end is uncovered, or covered by a permeable material, such as a permeable membrane. Preferably, the open end of the receptacle is substantially covered with a permeable membrane 4. The membrane 4 serves to prevent dust or other contaminants from entering the receptacle, and helps to keep any electro-active substance which might be inserted into the receptacle in position.

The membrane 4 is preferably made of a material through which the sample to be tested can pass. For example, if the sample is a blood sample, the membrane should be permeable to blood. Suitable materials for use as the membrane include polyester, cellulose nitrate, polycarbonate, polysulfone, microporous polyethersulfone films, PET, cotton and nylon woven fabrics, coated glass fibres and polyacrylonitrile fabrics. These fabrics may optionally undergo a hydrophilic or hydrophobic treatment prior to use. Other surface characteristics of the membrane may also be altered if desired. For example, treatments to modify the membrane's contact angle in water may be used in order to facilitate flow of the desired sample through the membrane. The membrane may comprise one, two or more layers of material, each of which may be the same or different. For example, conventional double layer membranes comprising two layers of different membrane materials may be used.

The membrane may also be used to filter out some components of the sample which are not desired to enter the cell. For example, some blood products such as red blood cells or erythrocytes may be separated out in this manner such that these particles do not enter the cell. Suitable filtration membranes, including blood filtration membranes, are known in the art. An example of a blood filtration membrane is Presence 200 of Pall filtration.

The electrochemical cell of the invention contains a working electrode 5 which is situated in a wall of the receptacle. The working electrode is, for example, in the form of a continuous band around the wall(s) of the receptacle. The thickness of the working electrode is typically from 0.01 to 25 μm, preferably from 0.05 to 15 μm for example 0.1 to 20 μm, more preferably from 0.1 to 10 μm. Thicker working electrodes are also envisaged, for example electrodes having a thickness of from 0.1 to 50 µm, preferably from 5 to 20 µm. The thickness of the working electrode is its dimension in a vertical direction when the receptacle is placed on its base. The working electrode is preferably formed from carbon, palladium, gold or platinum, for example in the form of a conductive ink. The conductive ink may be a modified ink containing additional materials, for example platinum and/or graphite. Two or more layers may be used to form the working electrode, the layers being formed of the same or different materials. For example, a layer of Ag/AgCl may be present beneath the working electrode layer.

The counter electrode 6 typically forms at least a part of either the base or the top of the receptacle, although the counter electrode may also be present in the wall or walls of the receptacle. In the present embodiment, the counter electrode 6 forms the base of the receptacle. The counter electrode is typically made from $Ag/AgSO_4$, carbon, Ag/AgCl, palladium, gold, platinum, $Cu/CuSO_4$, $Hg/HgCl_2$ or $Hg/HgSO_4$. It is preferably made from carbon, Ag/AgCl, palladium, gold, platinum, $Cu/CuSO_4$, $Hg/HgCl_2$ or $Hg/HgSO_4$. Each of these materials may be provided in the form of a conductive ink. The conductive ink may be a modified ink containing additional materials, for example platinum and/or graphite. Typically, the electrochemical cell of the invention contains only one counter electrode.

The counter electrode 6 typically has a surface area which is of a similar size to, or which is larger than, for example substantially larger than, that of the working electrode 5. Typically, the ratio of the surface area of the counter electrode to that of the working electrode is at least 1:1, such as at least 5:1, 10:1, preferably at least 20:1, more preferably at least 25:1. The counter electrode may, for example, be a macro-electrode. Preferred counter electrodes have a dimension of 0.01 mm or greater, for example 0.1 mm or greater. This may be, for example, a diameter of 0.1 mm or greater. Typical areas of the counter electrode are from 0.001 $mm^2$ to 10 $mm^2$, preferably about 5 $mm^2$. The minimum distance between the working electrode and the counter electrode is preferably from 10 to 1000 µm, for example from 10 to 300 µm.

In a typical cell according to the invention, each electrode will be separated from the neighbouring electrode by a distance of from 10 to 1000 µm, for example from 50 to 200 µm or from 75 to 150 µm. In order that the cell can operate, the electrodes must each be separated by an insulating material 7. The insulating material is typically a polymer, for example, an acrylate, polyurethane, PET, polyolefin, polyester or any other stable insulating material. Polycarbonate and other plastics and ceramics are also suitable insulating materials. The insulating layer may be formed by solvent evaporation from a polymer solution. Liquids which harden after application may also be used, for example varnishes. Alternatively, cross-linkable polymer solutions may be used which are, for example, cross-linked by exposure to heat or UV or by mixing together the active parts of a two-component cross-linkable system. Dielectric inks may also be used to form insulating layers where appropriate.

The electrodes of the electrochemical cell may be connected to one another and to any required measuring instruments by any suitable means. Typically, the electrodes will be connected to electrically conducting tracks which are themselves connected to one another and to the required measuring instruments.

The cell of the present invention may contain an electro-active substance 8. The electro-active substance 8 may be any substance which is capable of causing an electrochemical reaction when it comes into contact with a sample. Thus, on insertion of the sample into the cell and contact of the sample with the electro-active substance, electrochemical reaction may occur and a measurable current, voltage or charge may occur in the cell.

The electro-active substance 8 comprises an electrocatalyst. Typically the electro-active substance 8 comprises an electrocatalyst and a mediator. A mediator is a chemical species that has two or more oxidation states of distinct electro-active potentials that allow a reversible mechanism of transferring electrons/charge to an electrode. The mediator reacts with the sample in the electrochemical reaction, the reaction being catalysed by the electro-catalyst. Typical examples of an electro-catalyst are enzymes, for example lactate oxidase, cholesterol dehydrogenase, lactate dehydrogenase, glycerol kinase, glycerol-m-phosphate oxidase and cholesterol oxidase. Ionic species and metal ions, for example cobalt, may also be used as the electrocatalyst. Examples of suitable mediators are ferricyanide, ferrocyanide and ruthenium compounds such as ruthenium (III) hexamine.

The electro-active substance 8 is typically inserted into the receptacle in such a position that the electro-active substance is not in contact with the working electrode. This ensures that fouling of the working electrode is minimised or avoided. The electro-active substance may be dried to ensure that it remains in position. In a preferred embodiment of the invention, the electro-active substance is pre-coated onto the substrate which forms the base of the receptacle. This may be done either by directly coating the electro-active substance onto a flat substrate, or by forming a well in the substrate and dispensing an electro-active substance into the well. Typically, the electro-active substance is then dried into position and the thus-coated substrate is joined to the walls of the receptacle. Where the electro-active substance is inserted into a well in the substrate, the well typically has a cross-section which is identical to that of the final electrochemical cell. Thus, the well creates the bottom part of the receptacle formed by the electrochemical cell. Where the counter electrode is on the base of the receptacle, the electro-active substance is pre-coated onto the counter electrode layer.

This embodiment has the advantage that the electro-active substance is kept remote from the working electrode at all times during manufacture of the cell. Contact between electro-active substance and working electrode is therefore minimised before the cell is used. This in turn minimises fouling of the working electrode.

In an alternative preferred embodiment, the electro-active substance is impregnated into a membrane which is placed onto the substrate either before or after, preferably before, the substrate is joined to the walls of the receptacle. The electro-active substance may equally be impregnated into the membrane 4 which covers the cell. This embodiment also avoids contact between the electro-active substance and the working electrode and minimises fouling.

The receptacle forming the micro-electrode of the present invention may, for example, contain one or more small air-holes in its base or its wall or walls (not depicted in FIG. 1). These holes allow air to escape from the receptacle when sample enters the receptacle. If such air-holes are not present, the sample may not enter the receptacle when it flows over the open end, or it may enter the receptacle only with difficulty. The air holes typically have capiliary dimensions, for example, they may have an approximate diameter of 1-25 µm. Typically, from 1 to 4 air holes may be present.

Embodiment 2

Figure 2:
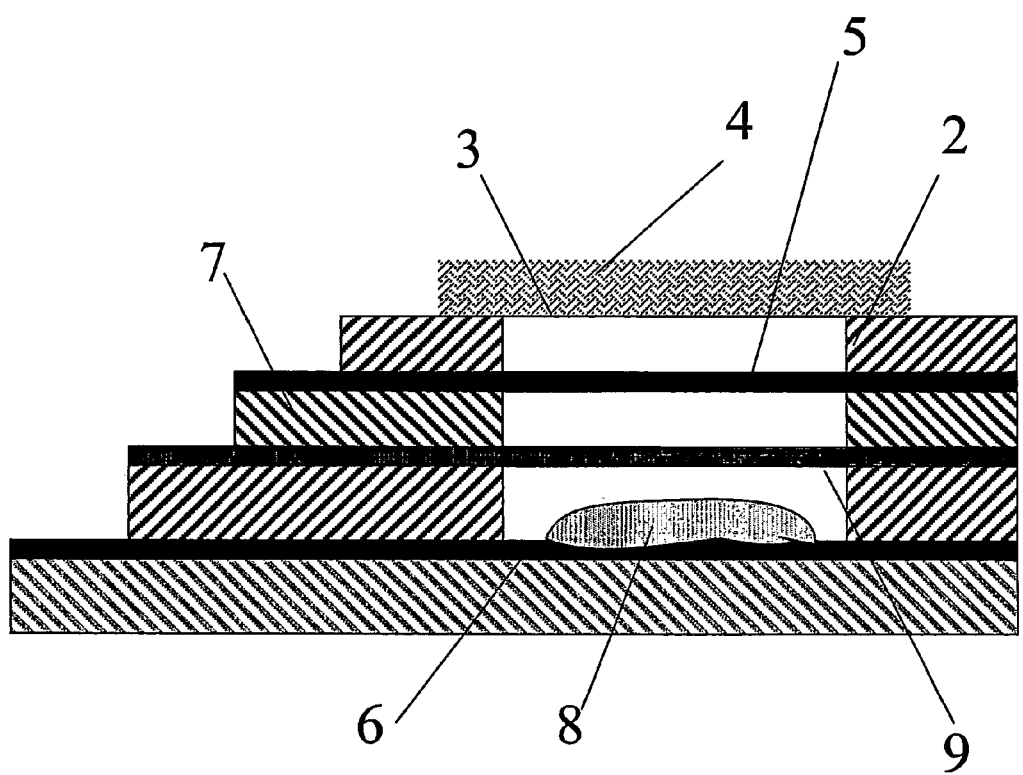
FIG. 2 depicts an electrochemical cell containing separate counter and reference electrodes in accordance with a second embodiment of the invention.

A second embodiment of the invention, which is the same as the first embodiment except as described below, is depicted in FIG. 2. In this embodiment, the cell contains one or more reference electrodes 9 in addition to the working and counter electrodes. In the case that no reference electrode is present (as in the first embodiment described above), the counter electrode acts as a reference or pseudo reference electrode. Typically, the reference electrode will be located in a wall of the receptacle 2. For example, the reference electrode may be in the form of a continuous band. The counter and working electrodes 6 and 5 may be positioned such that the reference electrode 9 is located between them, as is depicted in FIG. 2, or the counter and working electrodes 6 and 5 may be adjacent. The reference electrode is typically made from $Ag/AgSO_4$, carbon, $Ag/AgCl$, palladium, gold, platinum, $Cu/CuSO_4$, $Hg/HgCl_2$ or $Hg/HgSO_4$. It is preferably made from carbon, $Ag/AgCl$, palladium, gold, platinum, $Cu/CuSO_4$, $Hg/HgCl_2$ or $Hg/HgSO_4$. Each of these materials may be provided in the form of a conductive ink. The conductive ink may be a modified ink containing additional materials, for example platinum and graphite.

Embodiment 3

Figure 3:
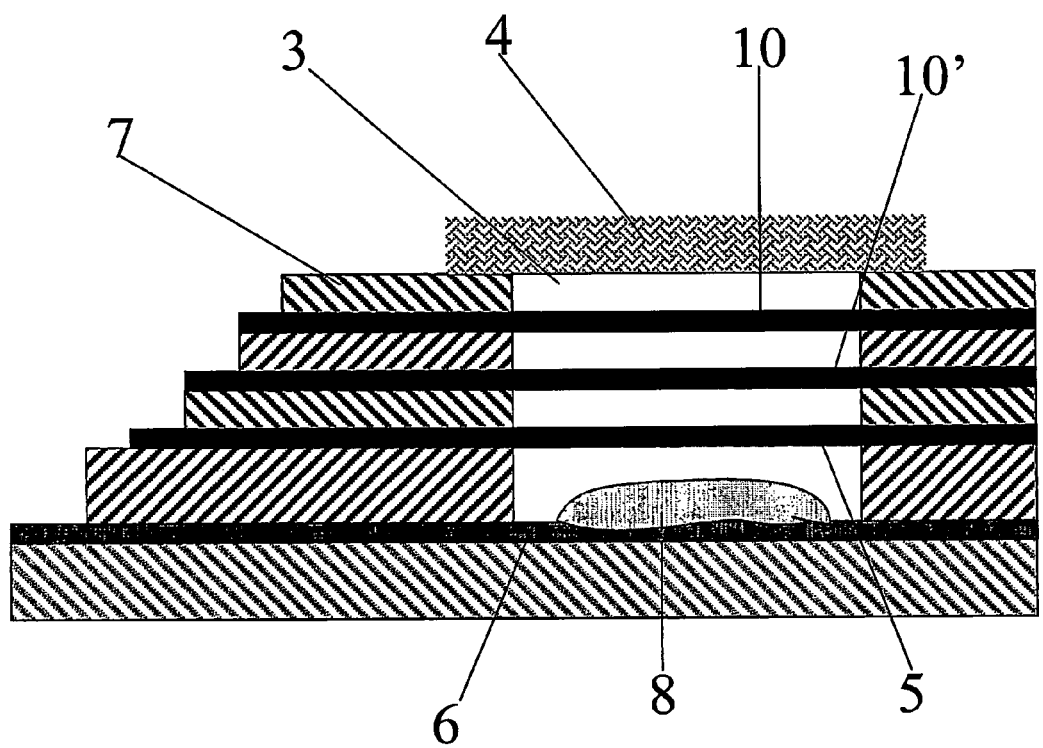
FIG. 3 depicts an electrochemical cell having multiple working electrodes in accordance with a third embodiment of the invention.

A third embodiment of the invention, which is the same as either the first or second embodiments except as described below, is depicted in FIG. 3. This embodiment of the invention is a multi-ring electrode which contains one or more further electrodes 10, 10' in addition to the working, counter and optionally reference electrodes. The one or more further electrodes 10, 10' typically act as additional working electrodes. Preferably, the counter electrode 6 acts as both the counter and the reference electrode and a separate reference electrode, as described in embodiment 2, is not present.

Typically, the receptacle comprises no more than 10 electrodes in total, including working, counter and reference electrodes. Preferably no more than 7 electrodes, more preferably no more than 5 electrodes are present. More preferred receptacles contain 2, 3 or 4 electrodes. Where more than one working and/or reference electrode is present, these are typically located one above the other in the wall(s) of the receptacle.

The additional working electrodes, 10, 10' allow different measurements to be carried out simultaneously on the same sample by applying different potentials across two or more of the working/counter electrode pairs. Alternatively, the same potential may be applied to each working electrode and the same measurement recorded several times for the same sample. This helps to eliminate or detect errors in the measurements taken.

In one particular example of this embodiment, one of the working electrodes is present on the base of the receptacle, i.e. in the position in which the counter electrode 6 is depicted in FIG. 3. In this case, the counter electrode is present either in the wall(s) of the receptacle as described below with reference to embodiment 5, or in the top of the receptacle as described below with reference to embodiment 4.

Embodiment 4

Figure 4:
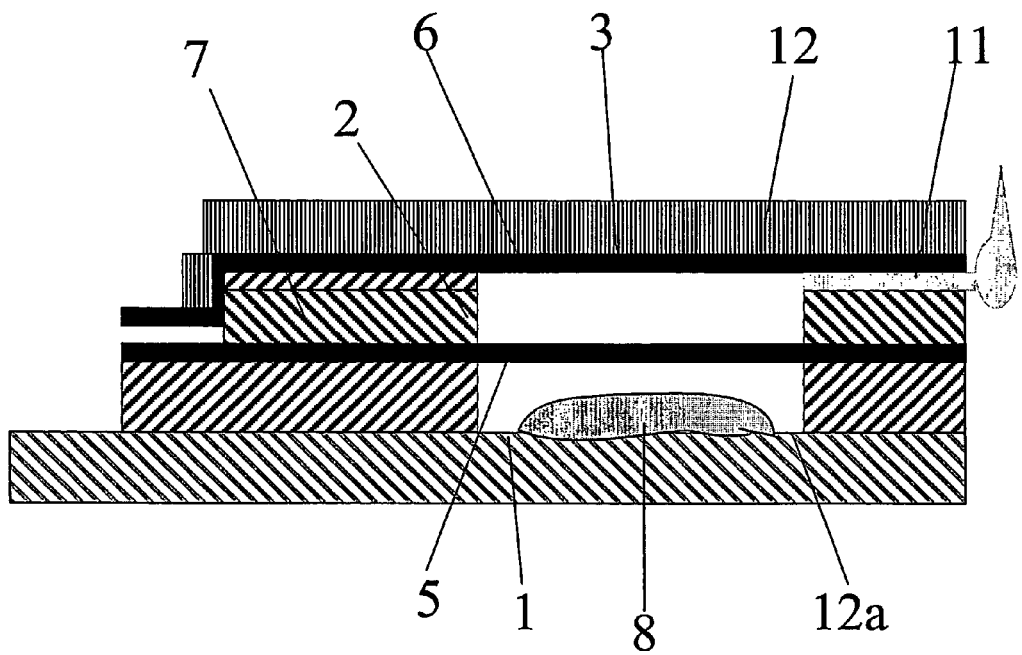
FIG. 4 depicts an electrochemical cell having capiliary flow channels in accordance with a fourth embodiment of the invention.

A fourth embodiment of the invention, which is the same as the first, second or third embodiments except as described below, is depicted in FIG. 4. In this embodiment, the cell comprises one or more capiliary channels 11 to allow sample to enter the receptacle. The capiliary channels are, for example, covered by a capiliary film. Examples of suitable capiliary films are PET films such as Melinex or ARcare®, adhesive coated films by Adhesive Research, and hydrophilic coated films such as ARcare® 8877, which can offer better capillary performance. In this embodiment, the receptacle is preferably covered by a substantially impermeable material 12. The impermeable material 12 is typically a capiliary film as described above. One or more capiliary channels 11 are provided, for example in a wall or walls of the receptacle 2, through which the sample may enter the receptacle. Typically, as is depicted in FIG. 4, the capiliary channel 11 is located at the point where the wall 2 meets the impermeable material 12.

In order that air can escape from the receptacle and allow the sample liquid to enter, one or more air holes must be present in this embodiment. Typically, an air hole will be positioned at the point where the base meets the wall of the receptacle, as indicated by the label 12a in FIG. 4. The air hole(s) preferably have the dimensions described above and preferably from 1 to 4 air holes are present.

This embodiment has the advantage that the top of the receptacle is closed and thus the counter electrode may either be located at the top 3, at the base 1; or in the wall(s) 2 of the receptacle. The counter electrode 6 is depicted at the top of the receptacle in FIG. 4. This is achieved by bonding the counter electrode 6 to the impermeable material 12 prior to its attachment to the receptacle. In this way, the electro-active substance 8, which is typically located on the base 1 of the receptacle, is not in contact with either the working or the counter electrodes and thus electrode fouling is significantly reduced or eliminated. It is possible to locate the electro-active substance on the top 3 of the receptacle, typically by pre-coating the substance onto the substrate which is to form the top 3 prior to its attachment to the receptacle.

A further advantage of placing the counter electrode at the top of the receptacle is that the base of the receptacle may be coated, or adapted in another way, to make it more suitable to receive the electro-active substance which is typically dried onto the base. For example, the base may be made of a particular material, such as carbon (provided that the carbon is electrically insulated from the electrodes), which is suitable for depositing enzymes on. Alternatively, the base may be coated with a hydrophilic coating.

If desired, the base of the cell may be formed from a permeable membrane which may be of the same type as the membrane 4 discussed above. The membrane is typically impregnated with an electro-active substance prior to, attachment to the cell. This avoids electrode-fouling caused by contact between electro-active substance and working electrode during insertion of the electro-active substance.

Embodiment 5

Figure 5:
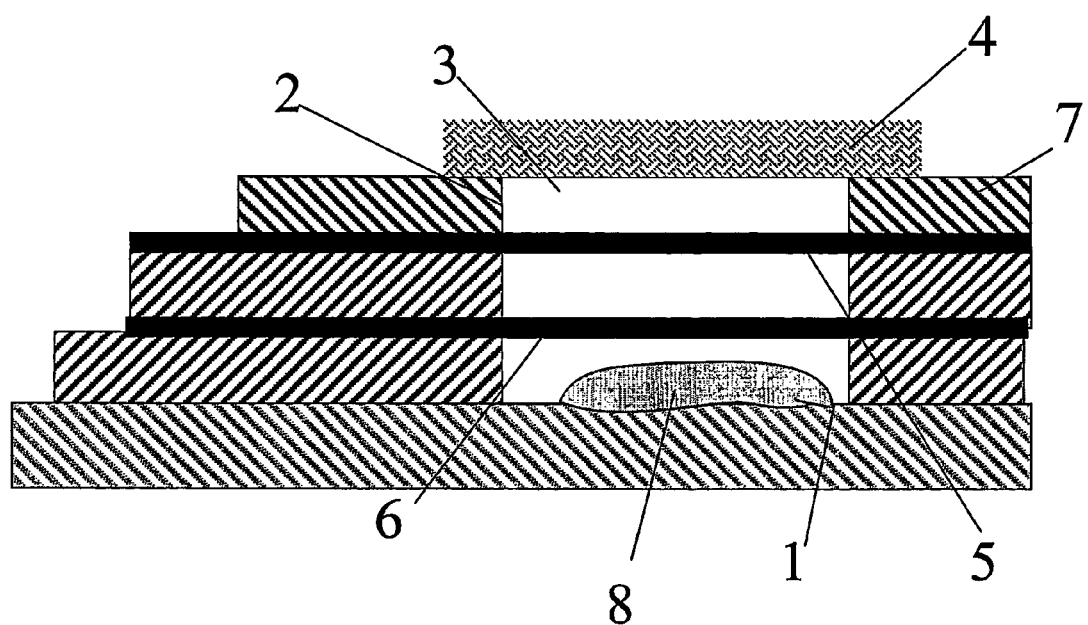
FIG. 5 depicts an electrochemical cell in which the counter electrode is in a wall or walls of the cell.

An alternative embodiment of the invention is depicted in FIG. 5. This embodiment is the same as any one of embodiments 1 to 4 discussed above except as described below. The counter electrode 6 in the cell of this embodiment is located in a wall or walls 2 of the receptacle. The counter electrode is, for example, in the form of a continuous band around the wall(s) of the receptacle.

The thickness of the counter electrode in this embodiment is typically from 0.1 µm to 1 mm, preferably from 5 to 500 µm, for example from 5 to 100 µm, more preferably from 5 to 50 µm. The thickness of the counter electrode in this embodiment is its dimension in a vertical direction when the receptacle is placed on its base. The ratio of the surface area of the counter electrode to that of the working electrode may, in this embodiment, be less than the preferred value of 25:1 which applies for counter electrodes located in the base or top of the receptacle. Preferred ratios for this embodiment are in the range 1:1 to 10:1, preferably 2:1 to 5:1.

Embodiment 6

Figure 6:
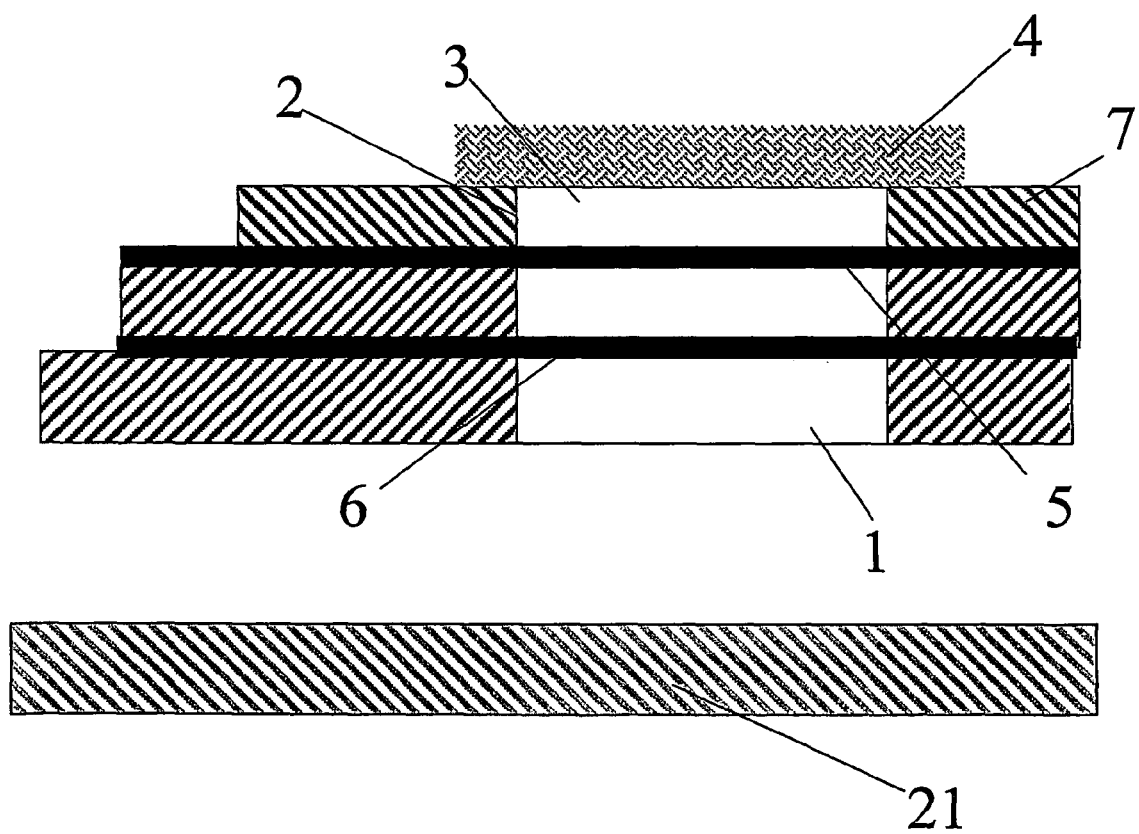
FIG. 6 depicts an alternative embodiment of the invention in which the cell itself is not in the form of a receptacle but forms a receptacle when placed on a substrate.

A further embodiment of the invention, which is depicted in FIG. 6, relates to a modification of the above described electrochemical cell in which the receptacle is completed when the cell is placed on a substrate 21. In this manner; the substrate 21 forms the base of the receptacle. The cell of this embodiment alone is not necessarily in the form of a receptacle since it has an opening at the position of the base 1. However, when placed onto a separate substrate 21, the cell together with the substrate forms a receptacle.

This embodiment therefore relates to a electrochemical cell comprising a counter electrode and a working electrode, wherein at least one electrode has a dimension of less than 50 μm, and wherein the cell has a shape such that, when placed on a substrate, the cell, together with the substrate on which it is placed, forms a receptacle, the working electrode being in a wall of the receptacle.

The electrochemical cell of this embodiment is at least partially open at its base 1. In this context, the term "open" includes a total absence of a base material and also the presence of a material which allows sample liquid to pass through it. Typically, the cell's base 1 is either at least partially uncovered or at least partially covered with a permeable membrane. The permeable membrane is optionally impregnated with an electro-active substance prior to its attachment to the walls of the receptacle.

The top of the cell 3 may be totally or partially covered with a permeable membrane 4 (as depicted) or with an impermeable material. If the cell is at least partially covered with an impermeable material, the counter electrode may be located at the top of the cell coated onto the impermeable material as described with reference to embodiment 4 above. This is achieved by bonding the counter electrode 6 to the impermeable material 12 prior to its attachment to the walls of the receptacle. An electro-active substance (not depicted), as described above, may also be bound to, the counter electrode prior to its attachment to the walls of the receptacle. If the cell is totally covered with an impermeable material, air-holes, as described with reference to embodiment 4, are preferably present in order to facilitate entry of a sample liquid into the cell. Alternatively, the counter electrode 6 may be located in the wall(s) of the cell as described in embodiment 5 above and as depicted in FIG. 6. Where the top of the cell 3 is open or covered only with a permeable membrane, the counter electrode is located in the wall(s) of the cell as here depicted.

The sample liquid to be tested enters the cell either through the top of the receptacle (where the top is not totally covered by an impermeable membrane), or, more usually, through the open base. This is typically achieved by placing the cell onto a substrate which is already coated with the sample liquid. Alternatively, the cell may be placed onto the substrate, either directly or through a permeable membrane, and the substrate then pierced within the receptacle in order to introduce a liquid sample present under the substrate surface into the receptacle. For example, the substrate may be the skin and the sample liquid blood. Alternatively, the substrate may be a pre-packaged container in which a sample liquid is present, the sample liquid being released when the container is pierced.

A non-limiting example of a use of the cell of this embodiment is as a self-testing blood analysis kit. A diabetic user for example might employ such a cell to carry out glucose analysis tests on samples of their blood. This can be done by (i) piercing the skin, e.g. a finger, which is optionally covered with a permeable membrane, (ii) placing the cell over the blood spot produced such that the skin, or the permeable membrane as relevant, together with the cell form a receptacle, and (iii) operating the cell in the usual manner. Alternatively, the cell may first be placed onto the skin or permeable membrane and the skin subsequently pierced through an open part of the receptacle. In the same manner, the cell can also be used for other types of blood test.

The remaining features of the cell are typically as described above with regard to the other embodiments of the invention.

Multi-Analyte Device

The present invention also provides a multi-analyte device which comprises two or more micro-electrodes of this invention, for example in accordance with any one of embodiments 1 to 6 above. The micro-electrodes of the multi-analyte device may each be of the same or different designs. Typical multi-analyte devices according to the invention are described in FIGS. 7, 8 and 9. The multi-analyte device will typically comprise a plate or strip 14 which contains one or more micro-electrodes 13a, b, c and d. Each micro-electrode may contain the same or different electro-active substances such that when a sample is inserted into each receptacle, several different tests may be carried out or the same test may be repeated several times in order to detect or eliminate errors in the measurements taken. Furthermore, the micro-electrodes may be set at different potentials, again providing different measurements for the same sample.

The micro-electrodes are typically separated by a distance of from 250 μm to 550 μm, for example from 250 μm to 425 μm.

A multi-analyte device can also be made with a "vertical" arrangement of cells as an alternative to Embodiment 3.

In this arrangement the sample in the first micro-electrode passes to a further micro-electrode below it, for example, using a permeable membrane in the base of the first micro-electrode, for a determination of a different component in the sample. The permeable membrane may be impregnated with an electro-active substance.

The electrical tracks 15 of the multi-analyte device are typically on the top surface of the device. Filled vias are used to connect the counter, optional reference and working electrodes to the surface tracks 15 which then mate with a measuring instrument 16, or the laminated back/counter can be arranged to mate with the instrument directly.

Figure 8:
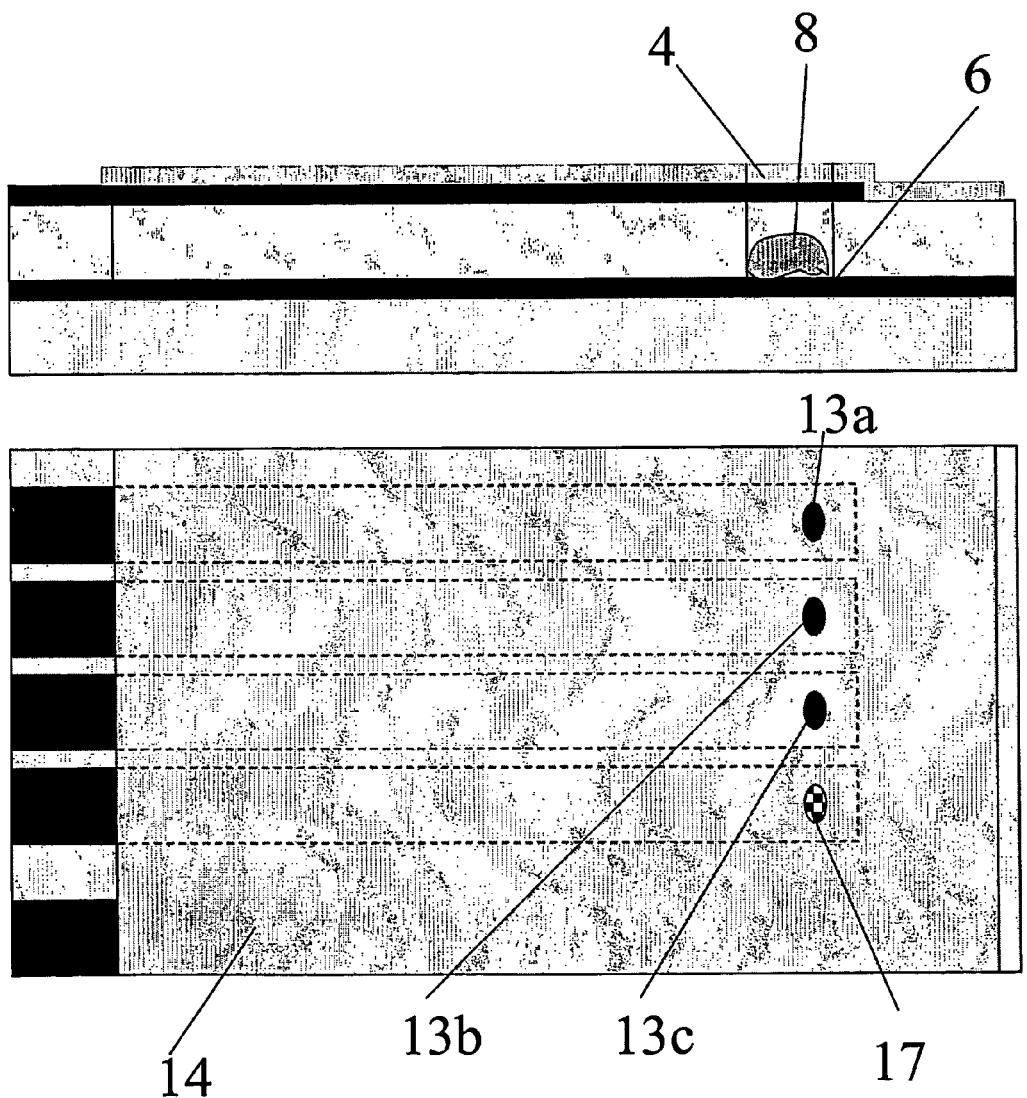

The multi-analyte device may contain one or more blank electrodes 17 as is depicted in FIG. 8. The blank electrode(s) do not contain a counter electrode. This embodiment may, for example, be useful where the electro-active substance has a working potential which conflicts with that of the counter electrode system. In this situation, reduction or oxidation of the mediator contained in the electro-active substance may occur. Thus, for example, where the counter electrode is a Ag/AgCl couple and the mediator is ferricyanide, the redox state of the mediator is such that it interacts with the Ag/ACl, forming a battery system or galvanic cell in which reactions occur spontaneously as soon as there is liquid connection between them.

The multi-analyte device may also comprise capillary channels 18 as are depicted in FIG. 9. These capillary channels are preferably of the type described in embodiment 4 above. Thus, each receptacle is provided with a capillary channel which may optionally be connected to a single channel from which the sample is drawn.

Process for Producing Electrochemical Cells

Figure 10:
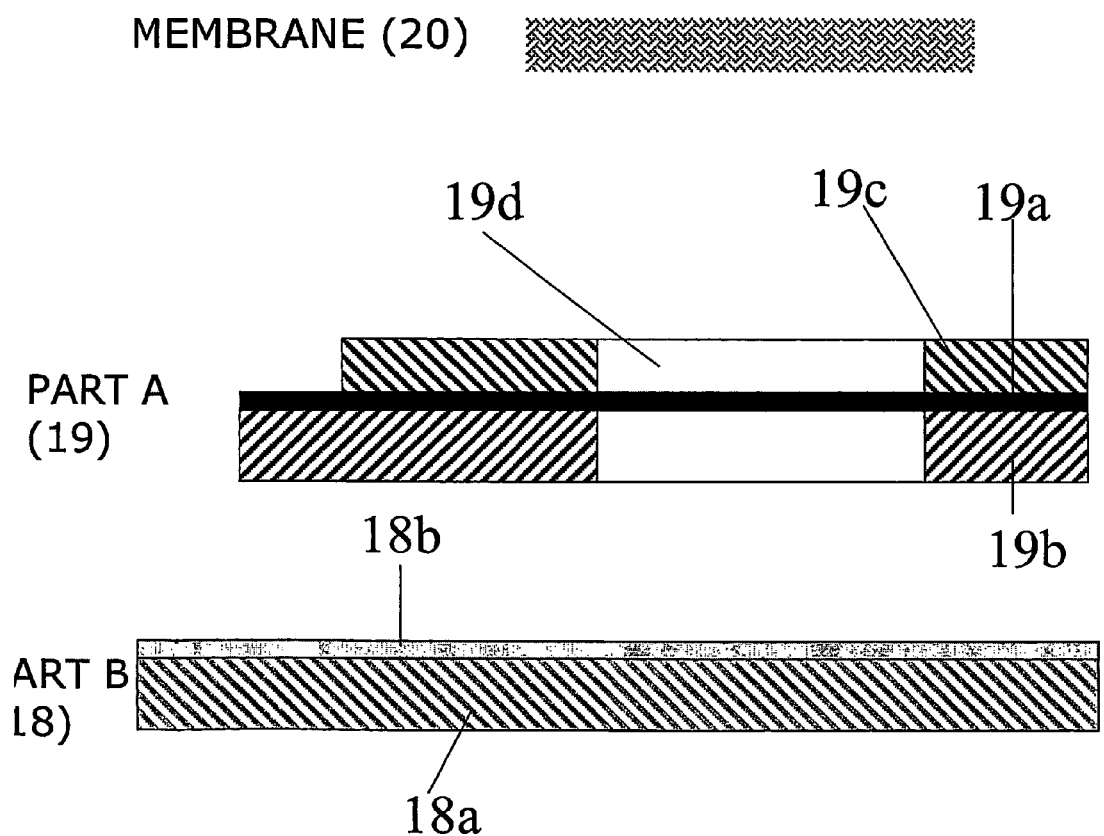
FIG. 10 illustrates a process for producing the electrochemical cells of the invention.

A process for producing the electrochemical cells of the first embodiment of the present invention is depicted in FIG. 10. The cells may be produced by a process which comprises the steps of:
(a) forming a first part 18 comprising an insulating material 18a which is optionally coated with a counter electrode layer 18b;
(b) forming a second part 19 comprising a laminate of a working electrode layer 19a between two layers 19b and c of an insulating material;
(c) creating a hole 19d in the second part; and
(d) bonding said first part 18 to said second part 19 to form a receptacle.

The materials, dimensions and other properties of the electrochemical cell are as described above.

Where the counter electrode is in the base of the receptacle, the first part comprises an insulating material 18a which is coated with a counter electrode layer 18b as depicted in FIG. 10. In this case, step (d) comprises bonding the counter electrode layer 18b of said first part 18 to said second part 19 to form a receptacle. Alternatively, when the counter electrode is in a wall or walls of the electrode as described in embodiment 5 above, the counter electrode layer may be absent from the first part and the second part comprises a counter electrode layer between two layers of insulating material.

Step (c) in which a hole is created in the second part may be carried out by any suitable means. For example, the hole may be punched or drilled or formed by die-cutting, ultra-sonic cutting or laser drilling. This step has the advantage that the electrode surfaces are automatically cleaned by the action of creating the hole, thus reducing the requirement for a separate step of cleaning the electrodes.

A suitable technique for creating the hole is to punch the second part with a pneumatic or hydraulic press tool. Holes of 0.1 to 5 mm, preferably 0.5 to 1.5, more preferably about 1 mm diameter are preferred. The hole should extend down through all of the printed layers and the substrate. The punching tool can be coated with hardening materials such as titanium and may or may not have an angled cutting edge. For example, the tool may be Ti coated with a 2° angle from the horizontal cutting edge.

The bonding step (d) may be carried out by any suitable bonding technique. For example, bonding may be performed using pressurized rollers. A heat sensitive adhesive may be used, in which case an elevated temperature is needed. Room temperature can be used for pressure sensitive adhesive.

If desired, air channels may be created in the micro-electrode at the joint between the first part 18 and the second part 19. This can be achieved, for example, by creating grooves in either the bottom side of the second part 19b or the top side of the first part 18a prior to bonding these two parts together.

Carbon or other inks may, for example, be printed onto the insulating material 18a, 19b, 19c using a screen printing, ink jet printing, thermal transfer or lithographic or gravure printing technique, for example the techniques described in GB 6106417.9. The insulating layer 19c may also be formed by printing an insulating material onto the working electrode layer. Other techniques for forming the insulating layer include solvent evaporation of a solution of the insulating material or formation of an insulating polymer by a cross-linking mechanism.

Each electrode is typically printed, or otherwise coated, onto the relevant insulating layer in a chosen pattern. For the working electrode or other electrodes which are to be formed in the wall of the receptacle, the pattern selected should be such that at least a part of the electrode layer is exposed when hole 19d is created. Preferably the pattern chosen is such that the electrode layer is exposed around the whole, perimeter of hole 19d.

In one embodiment, two or more printing or other coating steps are carried out to create an electrode layer. One or more steps, preferably one step, uses a pattern which deposits conductive material in the area which will form the perimeter of hole 19d as well as, for example, areas which are to form conductive tracks. This layer is exposed when hole 19d is created and forms the electrode. One or more further steps uses a pattern which deposits conductive material, for example, in areas which are to form conductive tracks but deposits no material in the area which will form the perimeter of hole 19d. These areas are not exposed when hole 19d is made. Thus, a thin electrode layer is formed around hole 19d, leading to a thin electrode in the wall of the finished receptacle, whilst a thicker layer is formed away from hole 19d. This thicker layer has a lower resistance and thus leads to a more efficient functioning of the electrochemical cell. This use of a double layer is particularly preferred with regard to the working electrode.

If desired, the one or more layers may be formed of different materials. For example, the layer which will be exposed at hole 19d may be formed of carbon whilst a further layer, for example a sub-layer, of a different material may be used.

The working electrode, counter electrode and reference electrode may all be produced by printing ink containing the desired material onto the substrate. Insulating layers may also be produced in this manner by printing an ink containing an insulating material onto a substrate or onto a conductive layer. Screen printing is a preferred manner in which this is carried out. Typically, a conductive layer will be printed onto a substrate and a dielectric layer will be printed onto the conductive layer.

Screen printing is generally carried out on polyester, polycarbonate, or other plastic/ceramic substrate. Types of substrates used are for example, DuPont films of Mylar A, Mylar ADS, Melinex, Kaladex, Tejin Tetoron, Purex, Teonex. Substrates used are preferably surface treated to improve adhesion of the ink to the substrate, for example by corona discharge or chemical modification. Substrates are also preferably laminated on one side, for example with either heat sensitive or pressure sensitive adhesive in the thickness range 20 μm to 200 μm, preferably about 40 μm. A preferred embodiment employs 250 μm thick Mylar ST535 with 40 μm thermally activated adhesive laminate as a substrate.

A screen is selected from stock with the carbon stencil defined with photosensitive emulsion with a thickness of 10 μm to 20 μm, preferably about 13 μm. The required thickness of the print is determined by the mesh count of the screen. Typically this is within the range of 83 t/inch to 330 t/inch, preferably 305 t/inch for both carbon Ag/AgCl inks, and about 195 t/inch for dielectric ink. The ink is typically forced through the mesh using a squeegee rubber of 65 to 85 shore hardness, preferably 75-shore hardness.

Suitable mesh counts are as follows:
Approx thickness of print when using 330 t/inch/=7 μm
   305 t/inch/120 t/cm=10 μm
   195 t/inch/77 t/cm=15 μm
   156 t/inch/61 t/cm=20 μm
   83 t/inch/=25 μm The printed layer is typically dried using the ink manufacturer recommendations. It is typically stoved in an oven for 2 minutes to 4 hours, preferably 1 hour, at about 70-130° C. Air drying, or air forced tunnel drying for 2-3 minutes at 90-130° C. may also be used.

The screen printed dielectric layer can be replaced by a laminate of polyester, polycarbonate or similar (preferably Mylar ST535) which covers the carbon layer and with thickness in the range 10 μm to 200 μm, preferably 10 μm to 30 μm.

Suitable inks for use in the screen printing processes are as follows:
Carbon Inks:
1. Coates carbon 26-8203
2. Ercon G449
3. Du-pont L881
Dielectric Inks:
1. Ronseal ultra tough hardglaze clear varnish.
2. Ercon E6165-116 blue insulator.
3. Du-Pont 5036 encapsulant
4. Coates screen flex coverlay.
Silver/Silver Chloride Inks:
1. Gem ag/agcl
2. Ercon E0430-128
3. Du-Pont 5874 conductor After forming the receptacle, an electro-active substance as described above may be inserted into the micro-electrode, for example, using micropipetting or enzyme jet printing. The electro-active substance may then be dried by any suitable technique. Alternatively, the electro-active substance may be pre-coated onto the base before bonding step (d) takes place. To achieve this, the electro-active substance is typically coated onto layer 18*b*, dried into position and subsequently parts 18 and 19 are bonded together as described above. A further option is to impregnate the electro-active substance into a membrane which can be placed on, or fixed onto, layer 18*b* prior to or after bonding step (d).

If desired, a permeable membrane may then be placed over the receptacle (as in FIG. 1). Membrane structures are applied to the top surface of the device using double sided adhesive or screen printed pressure sensitive adhesive. Attachment of the membrane 20 may, for example, be carried out by using a pressure sensitive adhesive (which has been cast) that has been die cut to remove the adhesive in the area over the receptacle. In the embodiments in which the electro-active substance is impregnated into membrane 4, impregnation of the desired substance is typically carried out before the membrane is attached to the receptacle.

If one or more capiliary channels are desired, these are preferably formed by creating one or more grooves in the top of the second part 19*c*, the grooves being connected to the hole 19*d*, or the top of the receptacle. The grooves may conveniently be created during the same process as creating the hole in the second part. For example, using a technique of pressing, punching, die-cutting, ultra-sonic cutting or other suitable film fabrication technique. The second part may then be coated with an impermeable material, for example a capiliary film as described above, thus creating a capiliary channel connected to the receptacle and which allows a sample to enter the receptacle.

Figure 11:
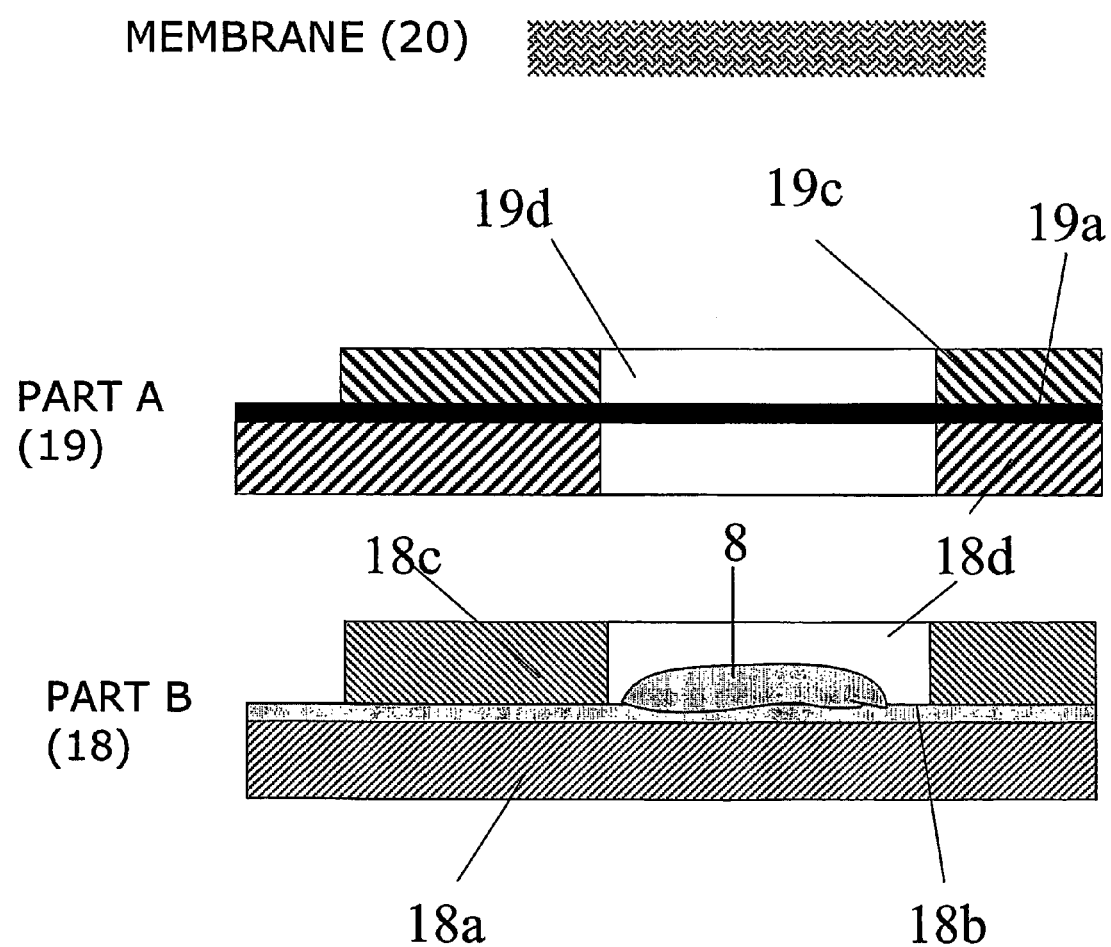
FIG. 11 illustrates a modified process for producing the electrochemical cells of the invention.

A modified process may be used when the electro-active substance is to be pre-coated into a well in the substrate which forms the base of the receptacle. This modified process is depicted in FIG. 11.

In this process, step (a) comprises, if desired, coating insulating layer 18*a* with counter electrode layer 18*b* as described above. A further insulating layer 18*c* is provided which has a pre-formed hole 18*d*. Hole 18*d* is typically of the same size as hole 19*d* and may be formed by the techniques mentioned above with reference to hole 19*d*. Insulating layer 18*c* is bonded to layer 18*b* thus creating a well in the position of hole 18*d*. An electro-active substance is then dispensed into this well, for example using micro-pipetting or enzyme jet printing. The electro-active substance may then be dried by any suitable technique. Following addition of the electro-active substance, Part B (18) may be used in bonding step (d) in the manner described above.

An alternative process may be used when the invention is to be produced in accordance with embodiment 4 above. In this embodiment, the process comprises the steps of:
  (a) forming a first part comprising an insulating material;
  (b) forming a second part comprising a laminate of a working electrode layer between two layers of an insulating material;
  (c) creating, in the second part, a hole and a capiliary channel to allow a sample to enter said hole;
  (d) bonding said first part to said second part to form a receptacle;
  (e) placing an electro-active substance as described above into the receptacle and optionally drying the electro-active substance; and
  (f) bonding to the open end of said receptacle a layer which is optionally coated with a counter electrode material.

The materials, dimensions and other properties of the electrochemical cell are as described above. Step (c), comprising forming a hole and a capiliary channel in the second part may be carried out as described above. In this process, the impermeable material or capiliary film is typically coated on the underside with a counter electrode material before it is bonded. Thus, when this layer is coated to the top of the receptacle, a counter electrode is formed. Alternatively, when the counter electrode is in a wall or walls of the electrode as described in embodiment 5 above, the counter electrode layer may be absent from the layer used in step (f) and instead the second part comprises a counter electrode layer between two layers of insulting material.

In a modification of the above process, the electro-active substance may be pre-coated onto either the base or the top of the receptacle by any desired technique, for example those discussed above, thereby eliminating the need for step (e). Thus, an alternative preferred process comprises steps (a), (b), (c), (d) and (f) above and employs (i) a first part which comprises an electro-active substance on its surface and/or (ii) a layer for use in step (f) comprising an electro-active substance its surface. Where said layer for use in step (f) comprises a counter electrode layer, the electro-active substance is typically coated onto the counter electrode layer. Following bonding step (f), a receptacle is thus formed having an electro-active substance coated to the interior surface of either the base or the top. If desired, the electro-active substance may be placed into a well in the substrate as discussed above in relation to FIG. 11.

In one embodiment, the insulating material of the first part is a permeable membrane as described above. The membrane is optionally impregnated with an electro-active substance prior to bonding step (d).

In order to form the electrochemical cell described in Embodiment 6 above, a modified version of any of the above described processes is used in which the step of bonding the first part to the second part is omitted. Thus, the process comprises:
  (a) forming a second part 19 comprising a laminate of a working electrode layer 19*a* between two layers 19*b* and *c* of an insulating material,
  (b) creating a hole 19*d* in the second part; and optionally
  (c) bonding to said second part a layer which is coated with a counter electrode material.

Steps (a) and (b) are carried out as described above with reference to corresponding steps. The process may optionally comprise a further step, which may be carried out before or after step (c), of attaching to the bottom of the second part a permeable membrane which may optionally have an electro-active substance impregnated into it. If the counter electrode is present in the top of the cell, step (c) above is carried out. If the counter electrode is present in a wall of the cell, step (c) may be omitted and the second part additionally comprises a layer of counter electrode material between two layers of insulating material.

An electro-active substance may be coated onto the counter electrode layer, if desired and alternatively or additionally to the electro-active substance bound to any permeable membrane present. This coating process may be carried out as described above.

In order to form the multi-analyte devices of the present invention, the step (c) described in one of the two processes above is extended to include the formation of two or more holes in the second part. Thus, when the bonding step (d) is carried out, two or more receptacles are formed. Where capiliary channels are used, these may be formed as described above at each of the receptacles. Thus, samples may be drawn into each micro-electrode by capiliary action.

Typical Uses of the Electrochemical Cell

The electrochemical cell of the present invention is intended principally for use as a micro-electrode for screening purposes, i.e. for screening liquid samples. For example, the cell may be used for determining the content of various substances in water, beer, wine; blood or urine samples, or samples of other biological or non-biological fluids. The cells may, for example, be used to determine the pentachlorophenol content of a sample for environmental assessment; to measure cholesterol, HDL, LDL and triglyceride levels for use in analysing cardiac risk, or for measuring glucose levels, for example for use by diabetics. A further example of a suitable use for the cells of the invention is as a renal monitor for measuring the condition of a patient suffering from kidney disease. In this case, the cells could be used to monitor the levels of creatinine urea, potassium and sodium in the urine.

Whilst the major use envisaged for the electrochemical cells of the invention is as a microsensor, the cells may also be used for any other purpose in which electrochemical measurement or the harnessing of electrochemical energy takes place. For example, the electrochemical cell of the invention may be used as a battery. The cell may also be used to process an electro-active substance such as an intercalating material used for detection of electrolytes such as sodium, potassium, calcium and phosphates. Such processing may involve electro-cycling of the substance in order to develop a consistent thin layer on the electrodes.

EXAMPLES

Example 1

Manufacture of Electrochemical Cell

A base film of 125 μm thick PET was printed with the counter/reference electrode using a silver/silver chloride printing ink, and then dried at 90° C. for 30 minutes.

A middle film of 250 μm PET was coated with heat seal. The film was then printed on the reverse side to the heat seal coating with a conductive carbon ink in a pattern that defines the conductive tracks. This was then dried at 90° C. for 1 hour. The carbon ink print was subsequently overprinted with a dielectric ink, except for the part of the tracks that were required to mate with the connector in the measuring instrument, where over printing was not carried out. The dielectric ink was then dried at 60° C. for 20 minutes.

Several holes were then formed in the middle layer using a punch that forms the holes using a shearing action. This punch comprised metal dies or pins having a diameter equal to that of the required holes. The metal dies or pins were used to shear the film which was supported by metal or wooden plates having holes that match the formation of the punch in order to allow the punch to slide.

Following punching of the holes, the middle film was laminated to the base film using heat. During the heating step, the heat seal on the underside of the middle film melts and bonds to the base film.

The desired electro-active substances were then dispensed into the wells formed. The substances were then dried using room temperature airflow over the surface.

Over some of the wells, a blood separation membrane was added that is capable of removing the larger cellular particles from whole blood. For these electrodes, a blood separation membrane such as Presence 200 by Pall filtration was attached to the top most surface of the electrodes covering the wells. Attachment of the membranes was accomplished by using a screen printed pressure sensitive adhesive cast around the wells onto the middle layer.

Example 2

Use of Electrochemical Cell

Electrodes were constructed from a 250 μm PET layer on which a 15 μm Coates carbon ink 26-8203 layer had been screen-printed followed by a 30 μm layer of Ronseal ultra tough hardglaze clear varnish (a polyurethane based on Baxenden trixine containing polyurethane and isocyanates). This layer was punched to produce a 1 mm diameter hole. A PET base layer was produced consisting of a 125 μm PET layer having a common Ag/AgCl counter reference on the top. The PET base layer was then adhered to the punched layer using ARcare 7841 sheet adhesive. Various tests were carried out using this electrochemical cell as described below at Examples 2a to 2f.

Example 2a

Figure 12:
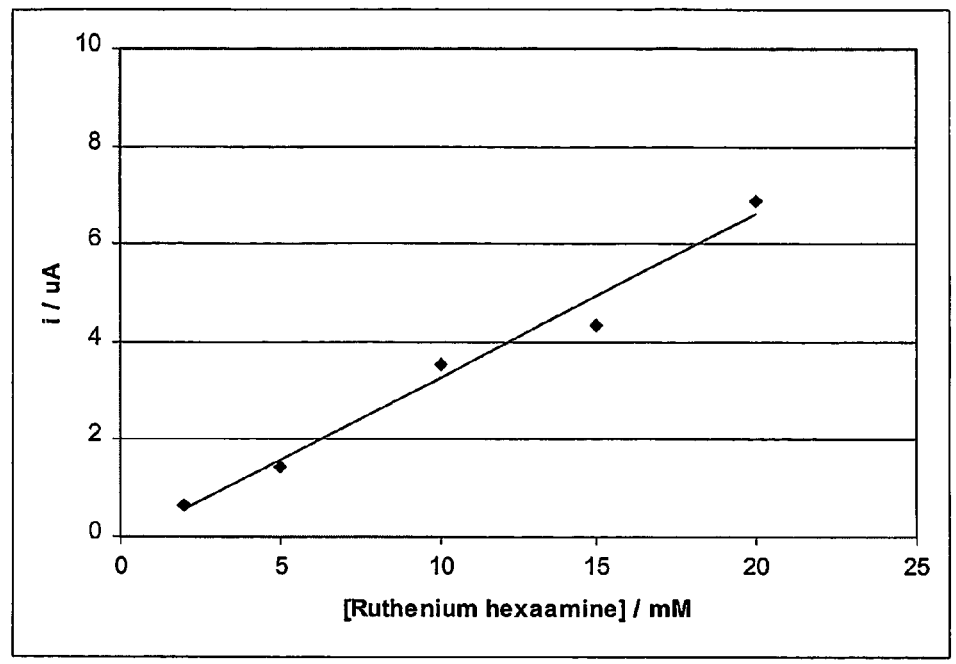
FIGS. 12 to 20 illustrate the results of amperometric and cyclic voltammetric experiments carried out using electrochemical cells according to the invention.

Cyclic voltammetric current was measured at −0.45 V vs. Ag/AgCl after addition of concentrations of 2, 5, 10, 15 and 20 mmol dm$^{-3}$ ruthenium hexaamine in 0.1 mol dm$^3$ Tris buffer at pH 9 containing 0.1 mol dm$^{-3}$ KCl. Results are shown in FIG. 12.

Example 2b

Figure 13:
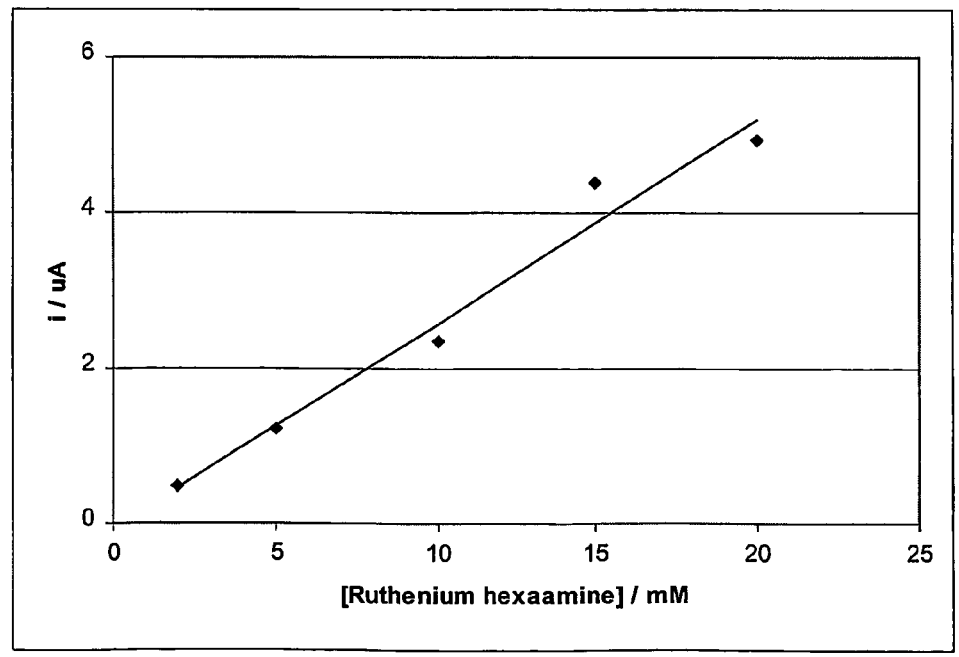

Amperometric current was measured 1 second after the application of a −0.50 V vs. Ag/AgCl potential step after addition of concentrations of 2, 5, 10, 15 and 20 mmol dm$^{-3}$ ruthenium hexaamine in 0.1 mol dm$^{-3}$ Tris buffer at pH 9 containing 0.1 mol dm$^{-3}$ KCl. Results are shown in FIG. 13.

Example 2c

Figure 14:
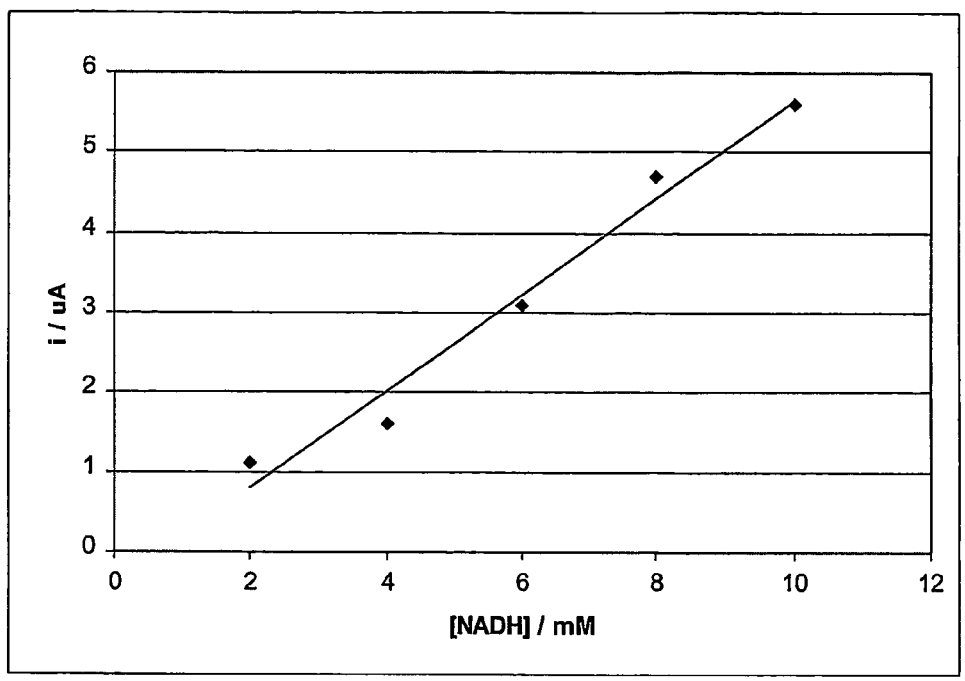

Cyclic voltammetric current was measured at 0.15 V vs. Ag/AgCl immediately after addition of 2, 4, 6, 8 and 10 mmol dm$^{-3}$ NADH in 0.1 mol dm$^{-3}$ Tris buffer at pH 9 containing 0.1 mol dm$^{-3}$ KCl to electrodes on which 0.2 mL of a solution containing 0.2 mol dm$^{-3}$ ruthenium hexaamine and 650 KU/mL putadiaredoxin reductase has been dried. Results are shown in FIG. 14.

Example 2d

Figure 15:
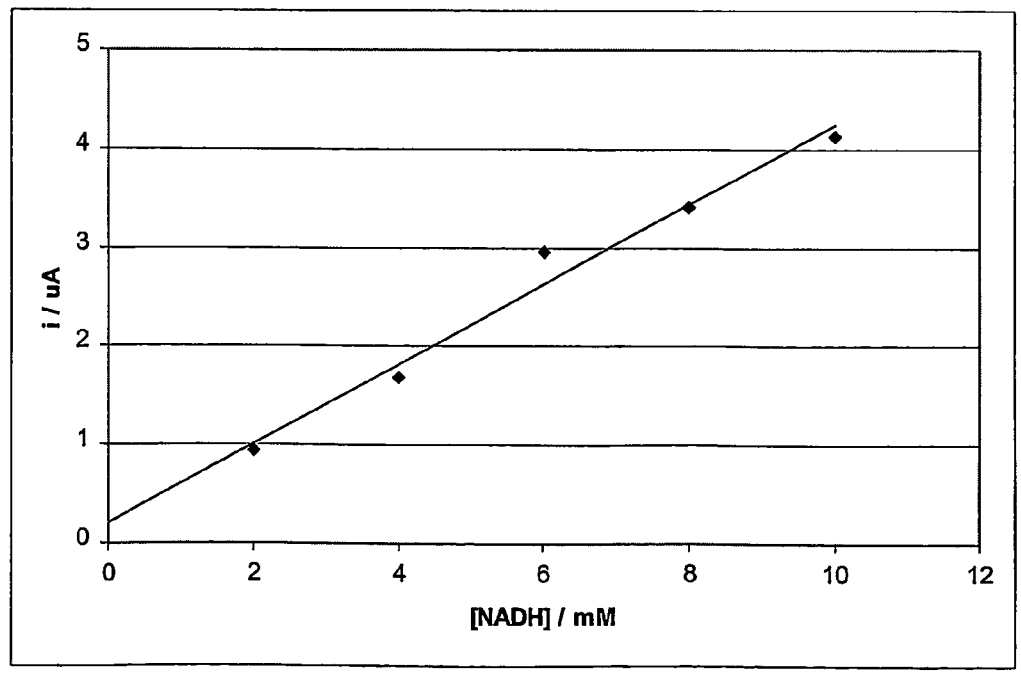

Amperometric current was measured 1 second after the application 0.15 V vs. Ag/AgCl on the addition of 2, 4, 6, 8 and 10 mmol dm$^{-3}$ NADH in 0.1 mol dm$^{-3}$ Tris buffer at pH 9 containing 0.1 mol dm$^{-3}$ KCl to electrodes on which 0.2 mL of a solution containing 0.2 mol dm$^{-3}$ ruthenium hexaamine and 650 KU/mL putadiaredoxin reductase has been dried. Results are shown in FIG. 15.

Example 2e

Figure 16:
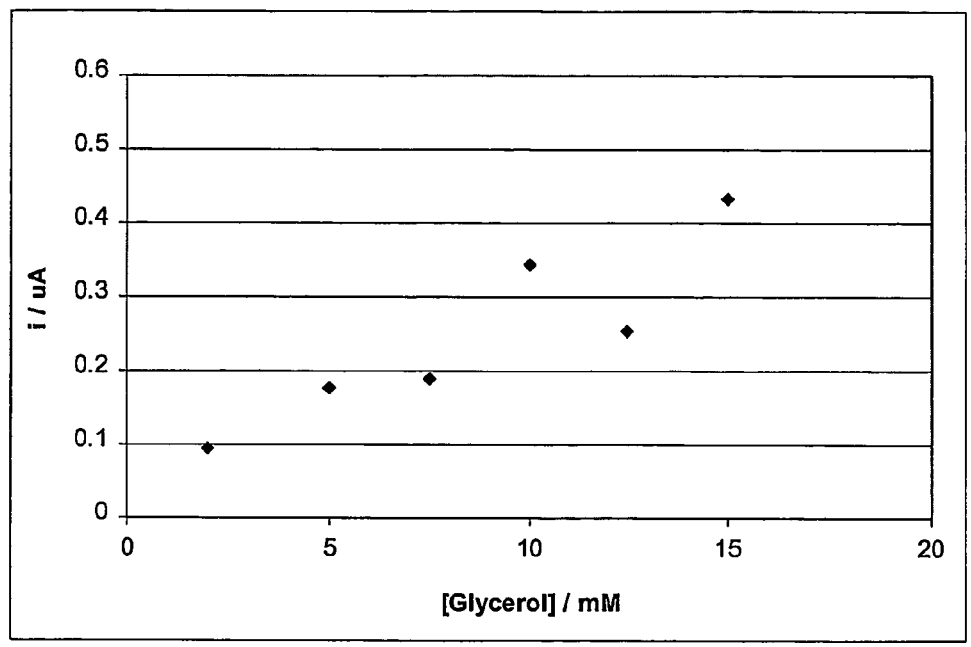

Amperometric current was measured 60 seconds after the application of a 0.20 V vs. Ag/AgCl potential step after addition of concentrations of 2, 5, 7.5, 10, 12.5 and 15 mmol dm$^{-3}$ glycerol in 0.1 mol dm$^{-3}$ Tris buffer at pH 9 containing 0.1 mol dm$^{-3}$ KCl obtained at electrodes on which 0.3 mL of a solution containing 150 U/mL glycerol dehydrogenase, 100 mmol dm$^{-3}$ of NAD, 100 mmol dm$^{-3}$ of ruthenium hexaamine, 100 mmol dm$^{-3}$ of ammonium sulphate, 100 mmol dm$^{-3}$ of potassium chloride has been dried. Results are shown in FIG. 16.

Example 2f

Figure 17:
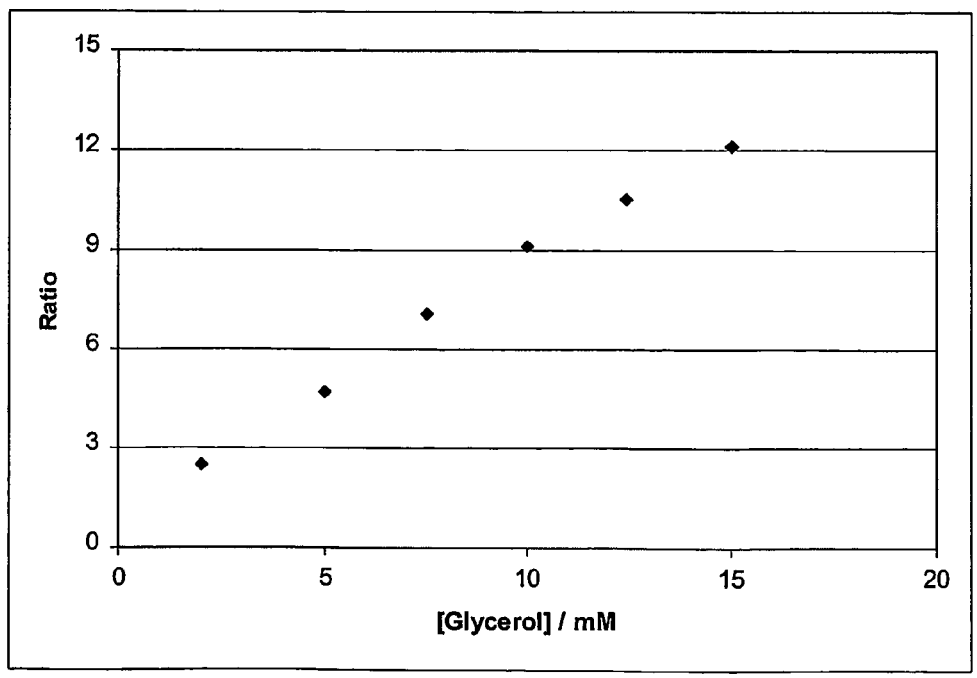

Ratio of amperometric current was measured 60 seconds after the application of a −0.50 V vs. Ag/AgCl potential step after addition of concentrations of 2, 5, 7.5, 10, 12.5 and 15 mmol dm$^{-3}$ glycerol in 0.1 mol dm$^{-3}$ Tris buffer at pH 9 containing 0.1 mol dm$^{-3}$ KCl obtained at electrodes on which 0.3 mL of a solution containing 150 U/mL glycerol dehydrogenase, 100 mmol dm$^{-3}$ of NAD, 100 mmol dm$^{-3}$ of ruthenium hexaamine, 100 mmol dm$^{-3}$ of ammonium sulphate, 100 mmol dm$^{-3}$ of potassium chloride has been dried. Results are shown in FIG. 17.

Example 3

Electrodes were constructed from a 250 μm PET layer on which a 7 μm Coates carbon ink 26-8203 layer had been screen-printed followed by a 30 μm Ronseal layer. This layer was punched to produce a 1 mm diameter hole. A base layer was formed by printing a 10 μm Ag/AgCl layer onto a 125 μm PET base layer. The base layer was then adhered to the punched layer using ARcare 7841 sheet adhesive. Various tests were carried out using this electrochemical cell which are described in Examples 3a and 3b below.

Example 3a

Figure 18:
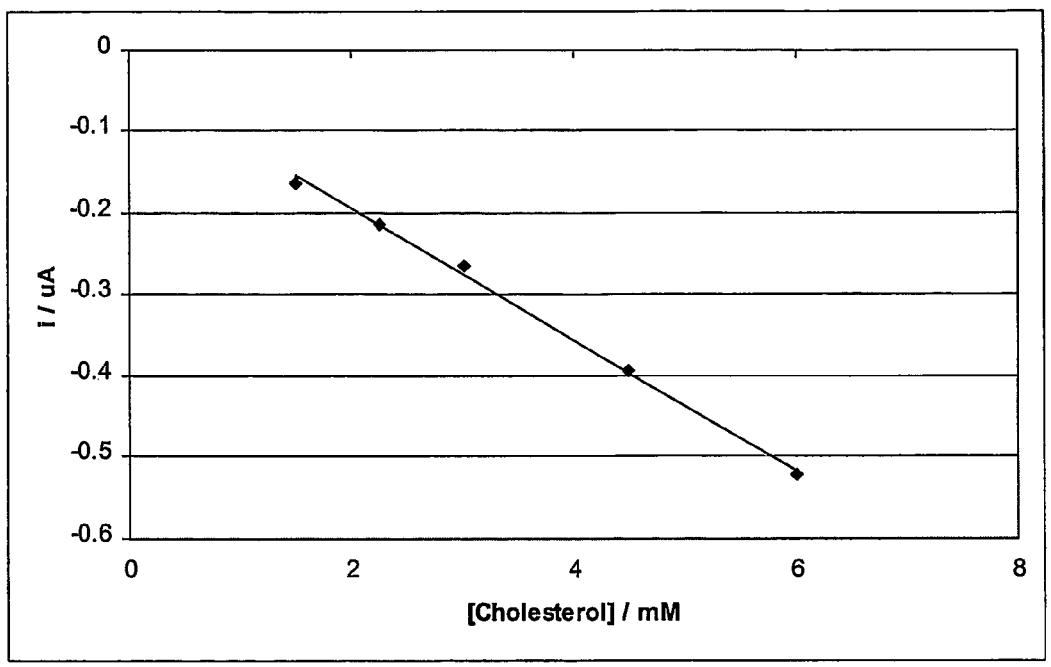

Amperometric current was measured 120 sec after the application of a −0.25 V vs. Ag/AgCl potential step. Showing the effect of additions of 1.5, 2.25, 3.0, 4.5, 6.0 mmol dm$^{-3}$ cholesterol to a solution comprising 1 KU/mL cholesterol oxidase, 200 KU/mL horseradish peroxidase, 33 mmol dm$^{-3}$ potassium ferrocyanide in 0.1 mol dm$^{-3}$ potassium phosphate buffer at pH 7.4 containing 0.1 mol dm$^{-3}$ KCl to electrodes with a common counter/reference electrode configured at the bottom of the well. Results are shown in FIG. 18.

Example 3b

Figure 19:
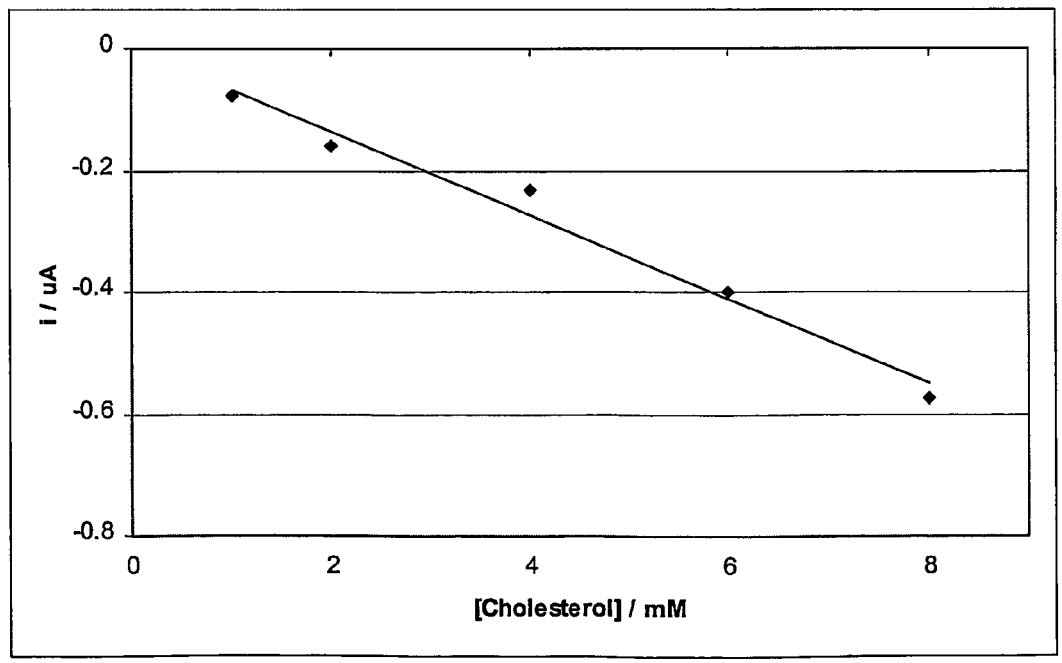

Amperometric current was measured 120 sec after the application of a −0.25 V vs. Ag/AgCl potential step. Showing the effect of additions of 1.5, 2.25, 3.0, 4.5, 6.0 mmol dm$^{-3}$ cholesterol to a solution comprising 1 KU/mL cholesterol oxidase, 200 KU/mL horseradish peroxidase, 33 mmol dm$^{-3}$ potassium ferrocyanide in 0.1 mol dm$^{-3}$ potassium phosphate buffer at pH 7.4 containing 0.1 mol dm$^{-3}$ KCl to electrodes with a common counter/reference electrode configured on the top of the strip. Results are shown in FIG. 19.

Example 4

Electrodes were constructed from a 250 μm PET layer on which a 7 μm Ercon carbon ink G449C layer had been screen-printed followed by a 30 μm Ercon E65615-116D dielectric layer. This was then punched to produce a 1 mm diameter hole. A 125 μm PET base layer was coated with a common Ag/AgCl counter reference layer (using Ercon E6165-128). The base layer as formed was then adhered to the punched layer using heat lamination.

Figure 20:
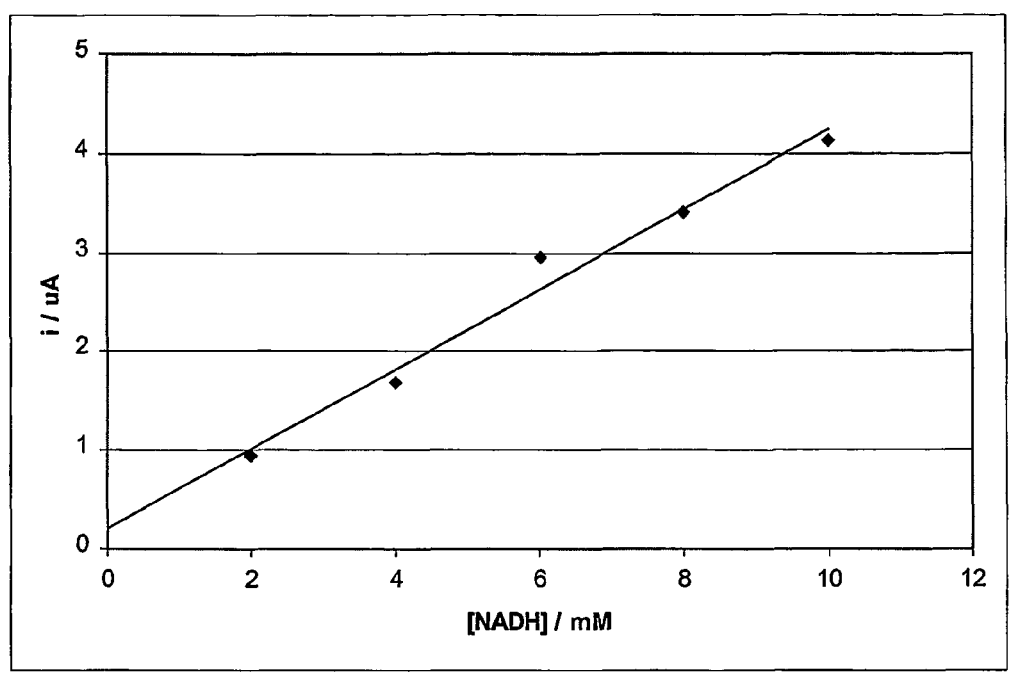

Amperometric current was measured 1 second after the application 0.15 V vs. Ag/AgCl on the addition of 2, 4, 6, 8 and 10 mmol dm$^{-3}$ NADH in 0.1 mol dm$^{-3}$ Tris buffer at pH 9 containing 0.1 mol dm$^{-3}$ KCl to electrodes on which 0.2 mL of a solution containing 0.2 mol dm$^{-3}$ ruthenium hexaamine and 650 KU/mL putadiaredoxin reductase has been dried. Results are shown in FIG. 20.

The invention claimed is:

1. An electrochemical cell in the form of a receptacle, said cell comprising a counter electrode and a working electrode, wherein the minimum distance between the working electrode and the counter electrode is 50 μm, wherein at least one electrode is a micro-electrode having one dimension of less than 50 μm and one dimension of greater than 50 μm, wherein the working electrode is in a wall of the receptacle, and wherein the receptacle contains an electro-active substance, and wherein the receptacle is shaped so as to restrict movement of the electro-active substance away from the electrodes when a sample flows over the electrochemical cell.

2. An electrochemical cell according to claim 1, wherein the working electrode is in the form of a continuous band.

3. An electrochemical cell according to claim 1, which further comprises a reference electrode.

4. An electrochemical cell according to claim 1, wherein the ratio of the surface area of the counter electrode to the surface area of the working electrode is at least 25:1.

5. An electrochemical cell according to claim 1, wherein the working electrode is a micro-electrode having at least one dimension in the range of 0.1 to 20 μm.

6. An electrochemical cell according to claim 1, wherein the receptacle has a width, or in the case of a cylindrical receptacle a diameter, of from 0.1 to 5 mm.

7. An electrochemical cell according to claim 1, wherein the minimum distance between the counter electrode and the working electrode is from 50 to 1000 μm.

8. An electrochemical cell according to claim 1, wherein a base and/or a wall or walls of the receptacle contain one or more air-outlet channels.

9. An electrochemical cell according to claim 1, wherein the electro-active substance has been dried.

10. An electrochemical cell according to claim 1, wherein the electro-active substance comprises an enzyme.

11. An electrochemical cell according to claim 1, wherein the base of the receptacle comprises an electro-active substance.

12. An electrochemical cell according to claim 1, wherein the base of the receptacle comprises a membrane, said membrane comprising an electro-active substance.

13. An electrochemical cell according to claim 1, wherein the open end of the receptacle is at least partly covered by a permeable membrane.

14. An electrochemical cell according to claim 13 wherein the permeable membrane comprises an electro-active substance.

15. An electrochemical cell according to claim 1, wherein the receptacle comprises one or more capillary flow channels through which a sample may enter.

16. An electrochemical cell according to claim 1, wherein the counter electrode forms at least a part of a base of the receptacle.

17. An electrochemical cell according to claim 15, wherein the receptacle is covered by a layer containing the counter electrode.

18. An electrochemical cell according to claim 1, wherein the counter electrode is in a wall or walls of the receptacle.

19. An electrochemical cell according to claim 1 which is suitable for screening liquid samples.

20. A multi-analyte device comprising a plurality of electrochemical cells according to claim 1.

21. A process for producing an electrochemical cell according to claim 1, which process comprises the steps of:
  (a) forming a first part comprising an insulating material which is optionally coated with a counter electrode layer;
  (b) forming a second part comprising a laminate of a working electrode layer between two layers of an insulating material;
  (c) creating a hole in the second part; and
  (d) bonding said first part to said second part to form a receptacle, which process further comprises placing an electro-active substance into the receptacle and optionally drying the electro-active substance, and wherein the receptacle is shaped so as to restrict movement of the electro-active substance away from the electrodes when a sample flows over the electrochemical cell.

22. A process according to claim 21 wherein the second part comprises a laminate of a counter electrode layer between two layers of insulating material.

23. A process according to claim 21 wherein the first part comprises an electro-active substance.

24. A process according to claim 21, which further comprises placing a membrane over at least a part of the open end of the receptacle.

25. A process according to claim 21, wherein step (c) comprises forming two or more holes in said second part, in order to form a multi-analyte device.

26. A process according to claim 21 which comprises the steps of:
  (a) forming a first part comprising an insulating material;
  (b) forming a second part comprising a laminate of a working electrode layer between two layers of an insulating material;
  (c) creating, in the second part, a hole and a capillary channel to allow a sample to enter said hole;
  (d) bonding said first part to said second part to form a receptacle;
  (e) placing an electro-active substance into the receptacle and optionally drying the electro-active substance; and
  (f) bonding to the open end of said receptacle a layer which is optionally coated with a counter electrode material.

27. A process according to claim 26, wherein step (c) comprises forming, in said second part, two or more holes and two or more capillary channels to allow a sample to enter said two or more holes, and wherein step (e) comprises inserting an electro-active substance, which may be identical or different, into one or more of the receptacles formed in step (d), in order to form a multi-analyte device.

28. A process according to claim 21, wherein one or more of the electrodes is formed by screen or inkjet printing onto a substrate.

29. A method of electrochemically testing one or more compounds of a sample, the method comprising the steps of:
  (a) providing an electrochemical cell in the form of a receptacle, said cell comprising a counter electrode and a working electrode, wherein the minimum distance between the working electrode and the counter electrode is 50 µm, wherein at least one electrode is a micro-electrode having one dimension of less than 50 µm and one dimension of greater than 50 µm, wherein the working electrode is in a wall of the receptacle, wherein the receptacle contains an electro-active substance, and wherein the receptacle is shaped so as to restrict movement of the electro-active substance away from the electrodes when a sample flows over the electrochemical cell;
  (b) inserting the sample into the electrochemical cell;
  (c) applying a voltage or a current between the working and counter electrodes; and
  (d) measuring the resulting current, voltage or charge across the working and counter electrodes.

30. A multi-analyte device comprising a plurality of electrochemical cells as defined in claim 13.

31. An electrochemical cell according to claim 1, wherein the ratio of the surface area of the counter electrode to the surface area of the working electrode is about 1:1.

32. An electrochemical cell according to claim 1, wherein the ratio of the surface area of the counter electrode to the surface area of the working electrode is from 1:1 to 25:1.

33. An electrochemical cell according to claim 1, wherein the working electrode is a micro-electrode having at least one dimension of less than 25 µm.

34. An electrochemical cell according to claim 1, wherein the receptacle has a width, or in the case of a cylindrical receptacle a diameter, of at least about 1 mm.

35. A process according to claim 21, wherein the step of creating a hole in the second part comprises a laser drilling step.

* * * * *

UNITED STATES PATENT AND TRADEMARK OFFICE
CERTIFICATE OF CORRECTION

PATENT NO. : 7,972,487 B2  
APPLICATION NO. : 10/499129  
DATED : July 5, 2011  
INVENTOR(S) : Hyland et al.

It is certified that error appears in the above-identified patent and that said Letters Patent is hereby corrected as shown below:

In column 3, line 7, change "insetting" to --inserting--.

In column 6, line 14, change "glycerol-m-phosphate oxidase" to --glycerol-III-phosphate oxidase--.

In column 6, line 18, change "ruthenium (111) hexamine" to --ruthenium (III) hexamine--.

In column 9, line 15, change "a" to --an--.

In column 11, line 57, change "6106417.9" to --0106417.9--.

Signed and Sealed this
Thirteenth Day of September, 2011

David J. Kappos  
*Director of the United States Patent and Trademark Office*